(12) United States Patent
Foster et al.

(10) Patent No.: US 12,396,884 B2
(45) Date of Patent: Aug. 26, 2025

(54) DEVICE AND METHOD FOR STIMULATING THE MEIBOMIAN GLANDS OF THE EYELID

(71) Applicant: Teeny Clean, LLC, Rancho Santa Fe, CA (US)

(72) Inventors: Robert M. Foster, Pagosa Springs, CO (US); John Olkowski, Honolulu, HI (US); Kirk Olkowski, Honolulu, HI (US); James Joseph Laux, Greensboro, NC (US); Clifford Hugh Price, San Diego, CA (US); Joel Douglas, Bonita Springs, FL (US)

( * ) Notice: Subject to any disclaimer, the term of this patent is extended or adjusted under 35 U.S.C. 154(b) by 469 days.

(21) Appl. No.: 16/852,829

(22) Filed: Apr. 20, 2020

(65) Prior Publication Data

US 2020/0330270 A1    Oct. 22, 2020
US 2025/0120850 A9    Apr. 17, 2025

Related U.S. Application Data

(63) Continuation-in-part of application No. 16/431,631, filed on Jun. 4, 2019, now abandoned, and a
(Continued)

(51) Int. Cl.
  *A61H 7/00*    (2006.01)
  *A46B 5/00*    (2006.01)
  (Continued)

(52) U.S. Cl.
  CPC ........ *A61F 9/00718* (2013.01); *A46B 5/0095* (2013.01); *A46B 9/005* (2013.01); *A46B 9/02* (2013.01); *A46B 11/001* (2013.01); *A46B 11/0093* (2013.01); *A46B 13/026* (2013.01); *A46B 13/04* (2013.01); *A61F 9/0008* (2013.01); *A61K 31/12* (2013.01); *A61K 31/616* (2013.01);
  (Continued)

(58) Field of Classification Search
  CPC .... A61H 35/02; A61H 2205/024; A61B 3/12; A61B 3/14; A61B 3/145; A61B 2017/00526; A61B 2017/00889; A61F 2007/0004; A61F 9/00772; A61F 9/00718; A61F 9/00745; A61M 2210/0612; A61K 45/09
  See application file for complete search history.

(56) References Cited

U.S. PATENT DOCUMENTS 4,883,454 A    11/1989 Hamburg
5,123,431 A *   6/1992 Wilson ................... A45D 40/28
                                                           132/320

(Continued)

FOREIGN PATENT DOCUMENTS

WO    WO2009066077       5/2009
WO    WO-2017200818 A1 * 11/2017 ............. A01N 33/00

*Primary Examiner* — Justine R Yu
*Assistant Examiner* — Christopher E Miller
(74) *Attorney, Agent, or Firm* — Joel Douglas; Thomas Ciesco; Jeffrey Semprebon

(57) ABSTRACT

The invention relates generally to the field of medical devices and, more specifically, to a handheld device that stimulates the meibomian gland of the eyelid mechanically, and specifically stimulates the meibomian glands of the eyelid to treat Meibomian gland dysfunction, also known as "Dry eye" and chronic marginal eyelid inflammation.

14 Claims, 24 Drawing Sheets

Related U.S. Application Data continuation-in-part of application No. 16/402,143, filed on May 2, 2019, now Pat. No. 11,166,871, which is a continuation of application No. 14/588,392, filed on Dec. 31, 2014, now Pat. No. 10,314,763.

(60) Provisional application No. 62/835,868, filed on Apr. 18, 2019, provisional application No. 62/011,591, filed on Jun. 13, 2014, provisional application No. 61/922,791, filed on Dec. 31, 2013.

(51) Int. Cl.
| | | |
|---|---|---|
| *A46B 9/00* | (2006.01) | |
| *A46B 9/02* | (2006.01) | |
| *A46B 11/00* | (2006.01) | |
| *A46B 13/02* | (2006.01) | |
| *A46B 13/04* | (2006.01) | |
| *A61F 9/00* | (2006.01) | |
| *A61F 9/007* | (2006.01) | |
| *A61K 31/12* | (2006.01) | |
| *A61K 31/616* | (2006.01) | |
| *A61K 45/06* | (2006.01) | |
| *A61B 17/00* | (2006.01) | |

(52) U.S. Cl.
CPC ...... *A61K 45/06* (2013.01); *A46B 2200/1006* (2013.01); *A61B 2017/00526* (2013.01); *A61B 2017/00889* (2013.01); *A61B 2017/00893* (2013.01); *A61B 2017/00955* (2013.01)

(56) References Cited

U.S. PATENT DOCUMENTS

| | | | | |
|---|---|---|---|---|
| 5,738,643 A | * | 4/1998 | Stredic, III | A61F 13/38 15/210.1 |
| 5,974,615 A | * | 11/1999 | Schwarz-Hartmann | A61C 17/3472 15/22.4 |
| 8,523,928 B2 | | 9/2013 | Korb et al. | |
| 9,802,062 B2 | * | 10/2017 | Bujak | A61N 7/00 |
| 2004/0015139 A1 | * | 1/2004 | La Bianco | A61M 35/003 604/289 |
| 2006/0104914 A1 | * | 5/2006 | Soroudi | A61F 9/0017 128/200.23 |
| 2006/0111485 A1 | * | 5/2006 | Laghi | C08K 5/01 523/122 |
| 2007/0186951 A1 | * | 8/2007 | Gueret | A45D 34/00 132/320 |
| 2008/0132978 A1 | * | 6/2008 | Korb | A61H 7/00 424/94.1 |
| 2009/0118702 A1 | * | 5/2009 | Lazar | A61F 9/0017 604/521 |
| 2011/0160635 A1 | * | 6/2011 | Baschnagel | A61M 35/006 15/104.94 |
| 2012/0065555 A1 | | 3/2012 | Walton et al. | |
| 2012/0165708 A1 | * | 6/2012 | Parsloe | A61H 15/00 601/18 |
| 2013/0018360 A1 | * | 1/2013 | Dockendorf | A61K 31/5575 604/290 |
| 2014/0052164 A1 | | 2/2014 | Rynerson | |
| 2014/0128780 A1 | * | 5/2014 | Kennedy | A61B 17/12118 604/20 |
| 2014/0214062 A1 | | 7/2014 | Rynerson | |
| 2014/0031845 A1 | | 11/2014 | Rynerson | |
| 2015/0127020 A1 | * | 5/2015 | Iwegbu | A45D 26/00 606/134 |
| 2015/0182415 A1 | * | 7/2015 | Olkowski | A61H 35/02 604/295 |
| 2015/0265825 A1 | * | 9/2015 | Miller | A61N 1/322 604/20 |
| 2016/0081455 A1 | * | 3/2016 | Shen | A45D 40/26 604/289 |
| 2017/0056241 A1 | * | 3/2017 | Shulman | A61M 35/003 |
| 2019/0133296 A1 | * | 5/2019 | Abadilla | A45D 40/26 |

* cited by examiner

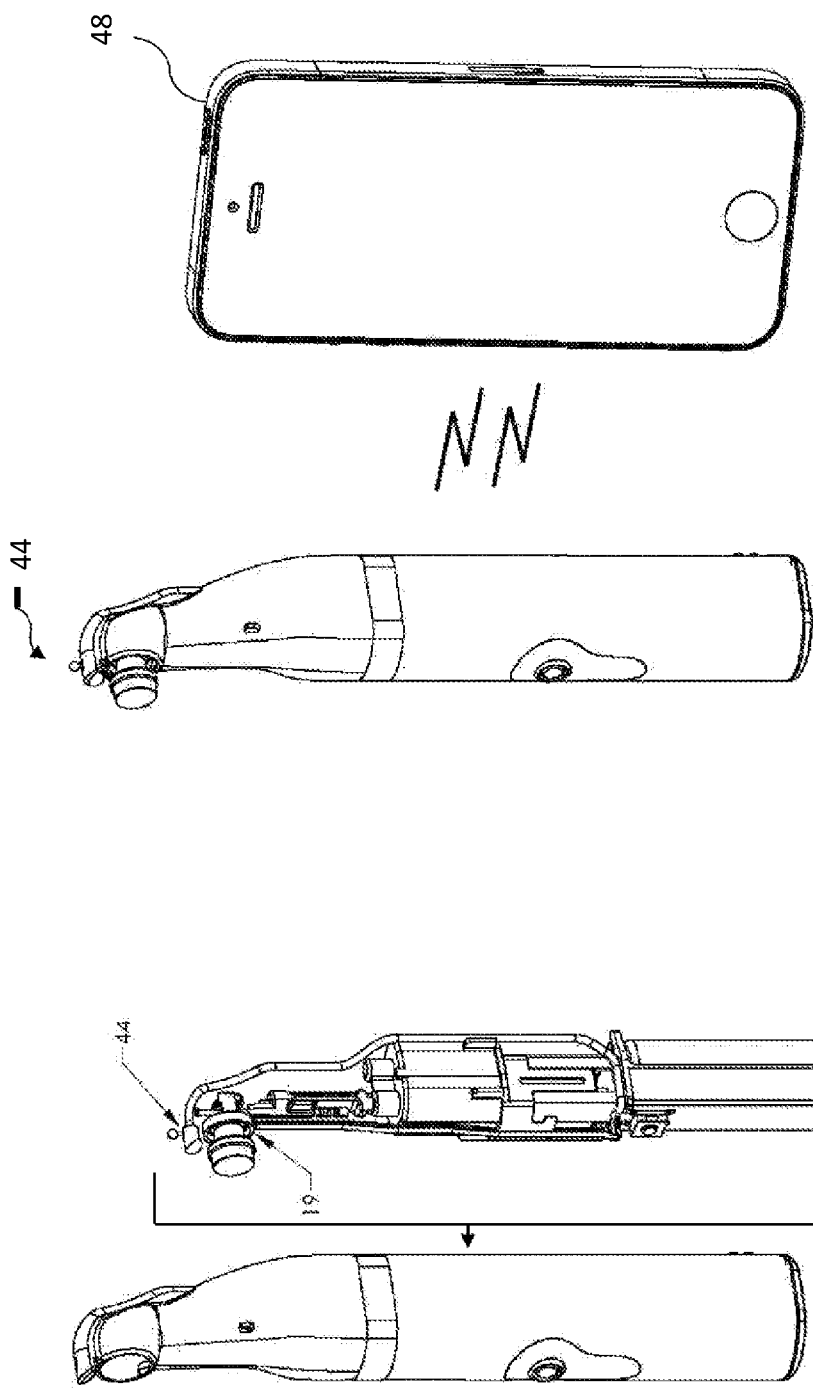

DEVICE AND METHOD FOR STIMULATING THE MEIBOMIAN GLANDS OF THE EYELID

CROSS-REFERENCE TO RELATED APPLICATION

This application claims priority from U.S. Provisional Patent Application No. 62/835,868, filed Apr. 18, 2019 entitled Device and method for stimulating the meibomian glands of the eyelid; this application claims priority from U.S. patent application Ser. No. 16/402,143, filed May 2, 2019, entitled Eyelid Care Appliance; this application claims priority from U.S. patent application Ser. No. 16/431,631, filed Jun. 4, 2019, entitled Eyelid Care Appliance, U.S. patent application Ser. No. 16/402,143 claims priority to U.S. patent application Ser. No. 14/588,392 now U.S. Pat. No. 10,314,763 issued on June 11 2019, U.S. patent application Ser. No. 14/588,392 now U.S. Pat. No. 10,314,763 claims the benefit of provisional patent application 62/011,591 filed Jun. 13, 2013, and U.S. patent application Ser. No. 14/588,392 now U.S. Pat. No. 10,314,763 claims the benefit of provisional patent application 61/922,791 filed Dec. 31, 2013, all of which are hereby incorporated by reference herein for all purposes.

COPYRIGHT STATEMENT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

Trademarks used in the disclosure of the invention and the applicants make no claim to any trademarks referenced.

BACKGROUND OF THE INVENTION

1) Field of the Invention

The present invention relates generally to the field of medical devices and, more specifically, to a handheld device that stimulates the meibomian gland of the eyelid mechanically.

2) Description of Related Art

For most people, once they develop meibomianitis, the condition lasts a lifetime. Untreated meibomian gland disease can lead to ocular infection and/or inflammation of the eyelids (referred to as posterior blepharitis). Posterior blepharitis, if untreated, can lead to corneal disease, which can lead to uncorrectable blurred vision and blindness, in severe cases.

Meibomian gland dysfunction, "Dry eye" and chronic marginal eyelid inflammation are widespread problems, especially in middle age and geriatric populations worldwide. In fact, "Dry eye" is the world's most common eye disease and the problem is so widespread that this topic is covered in virtually every ophthalmic medical textbook, and is the sole focus for groups of international researchers such as the Tear Film and Ocular Surface Society. "Dry eye" indicates the lack of quantity and/or quality of the tear film. In the human eye, the tear film covering the ocular surfaces is composed of three layers. The innermost layer in contact with the ocular surface is the mucus layer, comprised of many mucins. The middle layer, comprising the bulk of the tear film, is the aqueous (water) layer, and the outermost layer, is a thin (less than 250 nm) layer ("lipid layer") comprised of many lipids. The typical upper eyelid has about 25 meibomian glands and the lower eyelid has about 20 meibomian glands. The meibomian gland orifices open onto the eyelid margin at and around the junction of the inner mucous membrane and the outer skin of the eyelids; that junction is termed the mucocutaneous junction.

Dry eye disease is the result of a malfunction in the tear. Tears of the eye are made from different elements. The majority of the tear film is thin fluid that comes from the lacrimal gland, which is located directly above the eye. The quantity and quality of this fluid is usually not the problem. The meibomian glands, which are located throughout both the upper and lower eyelids and number in the range of twenty per lid, secrete an oily material (lipids), that keeps the watery part of tears (i.e., the fluid secreted by the lacrimal gland) from evaporating. This material is normally secreted/expressed with each blink. It is the dysfunction of these glands that is the problem for most people who suffer from dry eye conditions.

In individuals with healthy tear secretion, the oily material secreted by the meibomian glands is relatively warm and runny. As the normal human ages, the outflow of the meibomian glands decreases, thereby reducing tear contact time and causing a marked decrease in tear quality. In some individuals with long-stand meibomian gland dysfunction, secretions may cease altogether. As a result, the oily material that should have the consistency of olive oil, is instead semi-solid, like butter. When this happens, it is not easily secreted from the eyelid without being physically massaged.

The upward phase of blinking causes the upper eyelid to pull a sheet of the lipids secreted by the meibomian glands upward and over the other two layers of the tear film, thus forming a type of protective coating which limits the rate at which the underlying layers evaporate. Thus, a defective lipid layer or an incorrect quantity of such lipids can result in accelerated evaporation of the aqueous layer, which in turn, causes symptoms such as itchiness, burning, irritation, and dryness, which are collectively referred to as "dry eye". When left untreated, the consequences of dry eye can be severe, and even result in loss of vision (e.g., from desiccation of the corneal epithelium, ulceration and perforation of the cornea, or an increased incidence of infectious disease).

Dry eye states have many etiologies. A common cause of dry eye states is a disorder in which the glands are obstructed or occluded, usually referred to as "meibomian gland dysfunction" ("MGD"). Meibomian gland dysfunction is frequently the result of keratotic or biofilm obstructions which partially or completely block the meibomian gland orifices. Such obstructions compromise the secretory functions of the individual meibomian glands. More particularly, these obstructions can comprise combinations of bacteria, sebaceous ground substance, dead cells, and/or desquamated epithelial cells.

Additional causes of the dysfunction of the lipid layer are associated with eyelid margin inflammation (e.g., anterior and posterior blepharitis, hordeolum, sty, chalazion, and rosacea). The etiological factors of many of these inflammations include an overgrowth of bacteria (and/or parasites) and their toxic waste. These bacteria not only cause the lipid tear film to dysfunction, but they also destroy and block the very lipid-producing infrastructure by attacking the glands in the eyelid skin. Unfortunately, the particular types of bacteria and parasites that cause the inflammation/infections are common. The chance of having these on the eyelids is nearly 100%. By themselves, they are not dangerous, but it is the overgrowth of the biofilm and their toxic waste on the eyelid margin and the eyelashes, that must be avoided. Allowing the bacteria and parasites to proliferate must be prevented, especially if one is diagnosed as a dry eye sufferer.

While the tear film operates as a singular entity and all of the layers are important, the lipid layer, which is secreted from the meibomian glands, is of particular significance as it functions to slow the evaporation of the underlying layers and to lubricate the eyelid during blinking; such slowing of evaporation and lubrication of the eyelid largely prevent "dry eye syndrome and/or Ocular Surface Disease".

Thus, to summarize, the meibomian glands of mammalian eyelids (e.g., human), secrete oils that prevent evaporation of the tear film and provide lubrication to the eye and eyelids. These glands can become blocked or plugged by various mechanisms leading to so-called "dry eye syndrome and/or Ocular Surface Disease".

While not the only cause, meibomian gland dysfunction is believed to contribute to or be the primary cause of approximately 86% of dry eye syndrome. Dry eye syndrome is characterized by a blockage of the meibomian glands, which prevents normal lipid secretions from flowing from the meibomian glands to form the lipid layer of the tear film.

Various treatment modalities have been developed to treat the dry eye condition, including drops which are intended to replicate and replace the natural tear film, and pharmaceuticals which are intended to stimulate the tear producing cells. Various heating devices are commercially available that are designed to assist in unclogging the meibomian glands by liquifying accreted meidbum blockages of the meibomian glands. Other techniques involve manual expression of the glands and manual scrubbing of the eyelid margins, which are difficult for a patient to actually accomplish without assistance of a trained professional.

Eye drops such as REFRESH®, SOOTHE®, and SYSTANE® brand eye drops are designed to closely replicate the naturally occurring healthy tear film. However, their use and administration are merely a treatment of symptoms and not of the underlying cause. The effect of applying eye drops is short-lived. Further, the use of drops is generally for an indefinite length of time and consequently, extended use can become burdensome and costly.

Since dry eye is exacerbated by eyelid margin debris and bacterial overgrowth, daily eyelid hygiene is often prescribed by physicians and recommended by health institutions worldwide. This is for the life of the patient, because, as mentioned, dry eye is chronic, with no known cure. Unless proper eyelid hygiene is instituted, meibomian gland dysfunction will likely progress and dry eye syndrome will only worsen with age.

Herein lie the unsolved problems. The existence of a safe and easy to use eyelid care device that enables self-administered eyelid treatment using a motorized handpiece is needed. Currently the prior art motorized appliances are for clinical use. A second problem is the risk of patient injury during training of eyelid care professionals, and of lay persons who use a motorized eyelid care appliance for cleaning their own eyelids ("self-administered cleaning" or "SA Cleaning") or for cleaning others' eyelids ("second party cleaning" or "SP Cleaning"). The "second party" can be a pet (blepharitis is common in dogs and cats). A third problem is that the prior art eyelid care devices with motorized handpieces use unidirectional rotary tools (aka "heads") that become entangled with hair. A fourth problem is that eyelid care devices with rotary tools cause many patients to flinch when the tool first contacts the eyelid margin. Such flinching increases the risk of contact by the tool with the cornea, sclera, or other parts of the eye and resulting in laceration or other injury. A fifth problem is a lack of instrumentation of prior art motorized eyelid care devices, for which instrumentation (e.g., proximity monitoring, cleaning efficacy) and features (e.g., safety shutoff) would enable safer use of an eyelid care device as well as data collection and analysis of clinical signs and efficacy of cleaning.

Additionally, the ability to massage the meibomian glands while the eye is closed is beneficial to a majority of patients that have difficulty controlling the eyelid to allow direct stimulation of the meibomian glands.

People tend to wash their face, but not their eyelids. Eyelid hygiene should optimally be performed on a daily basis for maximum efficacy and optimal hygiene. Currently only manual scrubbing methods with cloths or fingers are available for daily home use, but such manual methods are like brushing one's teeth with a washcloth. Just as brushing one's teeth with a washcloth does not clean the gingival sulcus or mesio-distal aspects of teeth, an eyelid scrub typically contacts only the anterior ciliary margin and does not clean the entire confluence of the mucosal surface of the conjunctiva and the cutaneous epithelium. Even though daily eyelid hygiene is critically important for patients with an eyelid disease, there is typically no compliance by patients for whom SA Cleaning is ordered by their ophthalmologist. Due to a lack of alternatives, "baby shampoo" and a washcloth or cotton-tipped swab is often recommended by ophthalmologists for a patient's SA Cleaning. This current "prescription" for eye hygiene has significant non-compliance issues, i.e., patients fail to perform SA Cleaning. For instance, in a "baby shampoo regimen", the baby shampoo is mixed with warm or hot water in a prescribed ratio, and the solution is then applied with non-sterile applicators such as finger tips, cotton tips, or washcloths (typically, unsanitary). This results in an unsanitary process for the patient.

Although commercial "eyelid scrubs" are available in several forms, such as impregnated, pre-moistened towelettes or pads, or as bottled cleansers applied to a non-sterile applicator pad or to fingertips, such eyelid scrubs do not improve patient compliance or efficacy of the treatment. These rely on the individual to perform vigorous back and forth scrubbing of all four eyelid margins, which is cumbersome, time consuming, sometimes painful, and has uneven results. These factors are all strong disincentives to following an eyelid cleaning regimen.

Preventive and therapeutic interventions need to be more easily implemented at an earlier age or stage, of dry eye syndrome development, to decrease the likelihood of chronically scarred and/or dysfunctional meibomian glands. Lack of patient compliance is further evidenced by way of disproportionate commercial sales for eye care products. In contrast to the current US eyecare market for eye drops of $1 billion (excluding contact lens solutions), eyelid scrubs show less than $8 million in retail sales, which is a clear indication that people simply do not clean their eyelids.

Therefore, what is needed in the art is a system that is easy for the medical professional and patient to use to treat meibomianitis.

BRIEF SUMMARY OF THE INVENTION

The invention in one form is directed to a device which comprises of a power supply (e.g., battery), motor, detachable head, drive system that causes oscillation of the head, controls, instrumentation, and a housing. "Distal" means herein toward the end of the eyelid care appliance on which the head is mounted. "Proximal" means herein toward the end of the eyelid care appliance in which the power supply and motor are mounted.

The device is specifically designed and configured to massage the eyelids thereby eliminating any issue with damaging the eye by way of contact by the tool with the cornea, sclera, or other parts of the eye and resulting laceration or other injury.

A bristlehead or Soft-Tip that is detachably mated with the head receiver and protrudes from the housing along a second axis of the eyelid care appliance, the second axis being substantially perpendicular to the first axis, the bristlehead or Soft-Tip comprising a mount having a polygonal post configured to removably couple with a corresponding socket of the head receiver, the post and the socket oriented along the second axis, wherein friction between the post and the socket is configured to keep the bristlehead or Soft-Tip coupled to the head receiver during use. A bristlehead or Soft-Tip may be configured in a wide range of embodiments, some of which include various types of bristles, adjustable bristles, combinations of bristles and sponge, and other materials of varying topologies and degrees of abrasiveness.

A preferred embodiment of the eyelid care appliance is an "integral" eyelid care appliance comprising a power supply, motor, drive system that transmits motive force from the motor to oscillate a head receiver, motor controls, a proximity system, and proximity annunciator contained in a housing, wherein a bristlehead or Soft-Tip is detachably mated with the head receiver and protrudes from the housing and oscillates when the motor is powered on. A drive module (defined below) and an eyelid care module (defined below) are the principal elements contained in the housing. An alternate "two-piece" embodiment comprises a detachable neck that mates with a handpiece; the handpiece comprises the power supply, motor, and part of the drive system; the detachable neck comprises the head and remainder of the drive system. In a two-piece embodiment, the components of the eyelid care appliance can be distributed in whole or in part between the handpiece and the detachable neck, depending upon the component and configuration involved. As used herein, "handpiece" means the proximal portion of a two-piece embodiment of the invention, which proximal portion is gripped by a user.

An alternate "two-piece" embodiment of the eyelid care appliance comprises a handpiece and a detachable head and/or neck, a power supply, motor, proximity annunciator, and motor control being contained in the handpiece, a head receiver being contained in the neck and connected to the motor through a drive system with portions of the drive system distributed in the neck and in the handpiece and with a coupler at the interface of the handpiece and neck, which drive system transmits motive force from the motor to oscillate the head receiver, wherein a bristlehead or Soft-Tip is detachably mated with the head receiver, protrudes from the neck, and oscillates when the motor is powered on, and portions of a proximity system are distributed in the detachable neck and in the housing.

In the embodiments of the invention, the power supply (typically a replaceable and/or rechargeable battery) powers a DC motor, and when the motor is powered on, the motor (and drive translator, if the motor outputs unidirectional rotary motion, which motion is translated to oscillating motion) causes the oscillation of a driveshaft (or equivalent means of transmitting motive force, e.g., in a two-piece embodiment, an electric motor in a handpiece with magnetic or mechanical coupling to a detachable neck). The oscillating driveshaft causes the head receiver to oscillate, which causes the bristlehead or Soft-Tip mounted in the head receiver to oscillate. The eyelid care appliance is typically battery powered but can be powered by a power supply connected to an electrical outlet.

To use the eyelid care appliance claimed herein, a user grips the proximal portion of the appliance, powers on the appliance, and applies the oscillating head on the distal end of the appliance, together with a solvent or cleanser, to the eyelid to scrub the eyelid. In a preferred embodiment for SA Cleaning and SP Cleaning, the eyelid care appliance comprises a drive module, drive controls and annunciator, eyelid care module with adjustable head angle, proximity sensor, proximity controls and annunciator, and related data channels. A preferred configuration of proximity sensor and annunciator is a video camera, a Bluetooth®, or similar near field communication channel (Zigbee, Bluetooth, Bluetooth BLE, ANT+, WIFI, NFC or near field communications channel), and a smartphone or tablet computer with near field communications capability and display (collectively, "smart device"), that is paired with the eyelid care appliance. The video image from the eyelid care appliance is transmitted through the communication channel and displayed on the smart device. A user of the eyelid care appliance essentially "flies" the head onto the eyelid and moves the head across the eyelid. By focusing on the display, the user becomes immersed in control of the head rather than fearful of poking himself or herself in the eye. The proximity system can evaluate or score user performance as if the use of the eyelid care appliance were a video game. The interface between the device and smartphone application can monitor use of device, time, date, location and integrate the collected data through the smartphone application into the NSM portal for their reference and doctor compliance management.

Alternatively the instant invention for stimulating the meibomian glands of the eyelid comprising a handle/Main Housing; a head that is removable and neck and handle/Main Housing, the head comprising an bristlehead or Soft-Tip that oscillates to provide a massaging action to an eyelid and that comprises a front end that is concave in shape to fit over an eyelid; a heater located inside of the bristlehead or Soft-Tip; a temperature sensor located inside of the bristlehead or Soft-Tip, wherein the temperature sensor causes the bristlehead or Soft-Tip to heat to a predetermined temperature and then stop heating; and a charging base that supplies power to a motor that causes the bristlehead or Soft-Tip to oscillate, wherein the motor comprises a motor shaft.

In an alternative preferred embodiment, the device further comprises a switch that allows the bristlehead or Soft-Tip to oscillate with or without heating. Preferably, the handle/Main Housing comprises a light emitting diode that indicates to a user whether the batteries are being charged and whether the bristlehead or Soft-Tip is heating.

In yet another preferred embodiment, oscillation of the bristlehead or Soft-Tip is effectuated by an oscillation assembly located within the handle/Main Housing and comprising of a cam system which can be described as: a first stationary arm extending inward from an inner wall of the head; a rotating wheel that is connected to a rotating shaft that is in turn connected to the motor shaft; a second stationary arm extending inward from the inner wall of the head directly opposite the first stationary arm, the second stationary arm comprising a horizontal slot; and a connecting member with a first horizontal extension that is inserted into an aperture located off-center on the rotating wheel and a second horizontal extension that is inserted into the horizontal slot in the second stationary arm, wherein the connecting member comprises a center and pivots about a shaft that extends through an aperture in the center of the connecting member and that is fixedly attached to the bristlehead or Soft-Tip; wherein as the motor shaft rotates, the rotating shaft also rotates, causing the rotating wheel to rotate, the first extension on the connecting member to rotate in a circular motion, the second extension to move laterally within the slot on the second stationary arm, and the connecting member to pivot about the shaft that extends through the center of the connecting member, thereby causing the bristlehead or Soft-Tip to oscillate in an elliptical path.

In a preferred embodiment, the bristlehead or Soft-Tip further comprises a bristlehead or Soft-Tip cover that surrounds the front end of the bristlehead or Soft-Tip and that is comprised of a soft elastomer, thermoplastic elastomer, silicone or mixture of silicone and thermoplastic elastomer.

In a preferred embodiment, the bristlehead or Soft-Tip further comprises a bristlehead or Soft-Tip which is irreplaceably configured to attach and detach from the neck or handle/Main Housing and is capable of being held captive to the neck or handle/Main Housing by a magnet, clasp, cam, or locking mechanism.

In a preferred embodiment, the bristlehead or Soft-Tip further comprises a bristlehead or Soft-Tip which comprises of a soft elastomer, thermoplastic elastomer, silicone or mixture of silicone and thermoplastic elastomer or other soft plastic and has bristles surrounding a hollow cavity or recess on the head. The hollow cavity or recess on the head being centered on the primary axis through the center of the head face so as to facilitate the application of topical agents for liquids, gels, ointments, cleansers, solvents, gases, powders or other fluid or fluidizable medicaments deposited in the recess of the tip to be applied to the eyelid surface when the device of the invention is in use.

In a preferred embodiment, the bristlehead or Soft-Tip further comprises a bristlehead or Soft-Tip which comprises of a soft elastomer, thermoplastic elastomer, silicone, mixture of silicone and thermoplastic elastomer or other soft plastic and has an anti-inflammatory agent added to the matrix that makes up the bristlehead or Soft-Tip, such that the anti-inflammatory agent is applied to the eyelid surface when the device of the invention is in use.

In a preferred embodiment, the bristlehead or Soft-Tip further comprises a bristlehead or Soft-Tip which comprises of a soft elastomer, thermoplastic elastomer, silicone, mixture of silicone and thermoplastic elastomer or other soft plastic and has an anti-infective agent added to the matrix that makes up the bristlehead or Soft-Tip such that the anti-infective agent is applied to the eyelid surface when the device of the invention is in use.

In a preferred embodiment, the bristlehead or Soft-Tip further comprises a bristlehead or Soft-Tip which comprises of a soft elastomer, thermoplastic elastomer, silicone, mixture of silicone and thermoplastic elastomer or other soft plastic and has an aminoglycosides agent added to the matrix that makes up the bristlehead or Soft-Tip such that the aminoglycosides agent is applied to the eyelid surface when the device of the invention is in use.

In a preferred embodiment, the bristlehead or Soft-Tip further comprises a bristlehead or Soft-Tip which comprises of a soft elastomer, thermoplastic elastomer, silicone, mixture of silicone and thermoplastic elastomer or other soft plastic and has bristles surrounding a hollow cavity on the head so as to be able to massage the eyelid without damaging or irritating it wherein the cavity provides a reservoir that helps maintain lubricity during the treatment by capturing lubricant which would otherwise escape during operation.

In yet another embodiment, the present invention is a method for stimulating the meibomian glands of the eyelid comprising: providing a device with a handle/Main Housing and a head that is removable from the handle/Main Housing, the head comprising a bristlehead or Soft-Tip that oscillates to provide a massaging action to an eyelid; using a heater and temperature sensor located inside of the bristlehead or Soft-Tip to heat the bristlehead or Soft-Tip to heat to a predetermined temperature and maintain the bristlehead or Soft-Tip at the predetermined temperature; using a motor located inside of the handle/Main Housing and to cause the bristlehead or Soft-Tip to oscillate; and applying the bristlehead or Soft-Tip to an eyelid of a user.

It is therefore a primary objective of the invention to provide a means of massaging the eyelid to increase tear production of the meibomian gland and reduce the meibomian gland dysfunction.

BRIEF DESCRIPTION OF THE DRAWINGS

A further understanding of the nature and advantages of particular embodiments may be realized by reference to the remaining portions of the specification and the drawings, in which like reference numerals are used to refer to similar components. When reference is made to a reference numeral without specification to an existing sub-label, it is intended to refer to all such multiple similar components.

FIG. 12b: Bristle Head Side View
FIG. 12c: Bristle Head Isometric View
FIG. 13b: Bristle Head Side View
FIG. 13c: Bristle Head Isometric View
FIG. 18a: Eyelid Care Appliance with Video Proximity System.
FIG. 18b: Eyelid Care Appliance with Video Proximity System and Near Field Communication Channel to Smart Device.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION

Figure 1D:
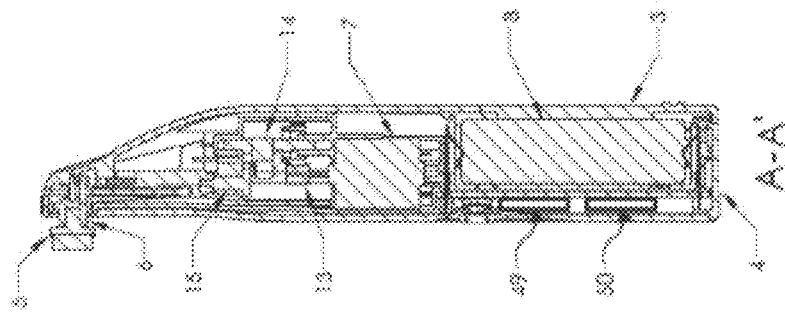
FIG. 1*d*: Eyelid Care Appliance, Integral Version, Cross-section View
Figure 1C:
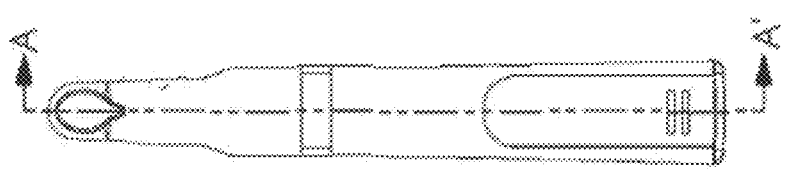
FIG. 1*c*: Eyelid Care Appliance, Integral Version, Rear View
Figure 1B:
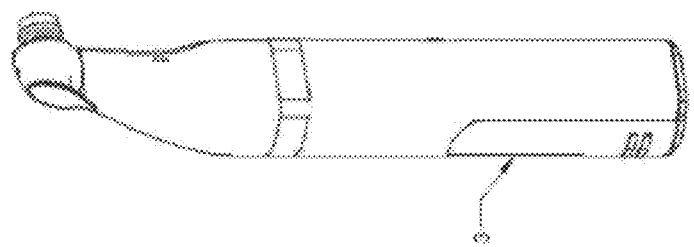
FIG. 1*b*: Eyelid Care Appliance, Integral Version, Rear Isometric View
Figure 1A:
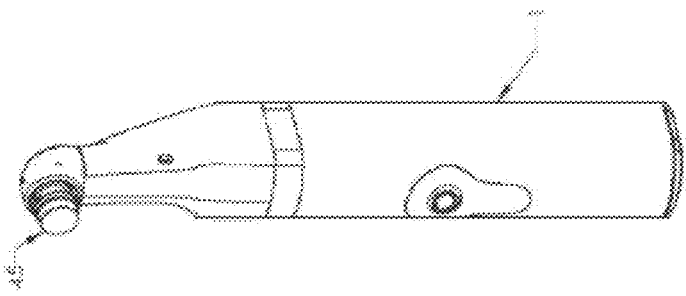
FIG. 1*a*: Eyelid Care Appliance, Integral Version, Front Isometric View

Given existing art methods and devices, it is not surprising that there is little or no compliance to eyelid hygiene by patients. Related art describes an "Eyelid and Anterior Orbit Swab" (to Hamburg, U.S. Pat. No. 4,883,454) and various eyelid cleansers, such as U.S. Pat. Nos. 8,535,736, 8,449,928, and 8,231,912 (to Gilbard), to clean the eyelids, but these rely solely on manual back and forth motion of a device on the eyelid margin and manual application of a cleanser, the entire contents all of which are hereby incorporated by reference.

A number of devices have been invented that apply compression to the anterior and or posterior surface of the eyelids, heat and/or apply electrical microcurrent or sonic energy (which the present invention does not do) to various parts of the body, but none of them is specifically tailored to address the problem of meibomian gland disease. For example, U.S. Pat. No. 4,387,707 (Polikoff, 1983), the entire contents all of which are hereby incorporated by reference, discloses an eye treatment device that applies a fluctuating massaging force against the eye through a flexible wall in a chamber that contains a fluid maintained under a fluctuating pressure. This device does not involve heating of the eyelid.

U.S. Pat. No. 4,918,818 (Hsieh, 1990), the entire contents all of which are hereby incorporated by reference, describes a multi-purpose shaver with a face massaging component. In order to use the face massaging component, the razor holder is detached from the body of the device, and the face massaging component is attached to the body of the device where the razor holder had been. This device does not involve a heating element.

U.S. Pat. No. 6,275,735 (Jarding et al., 2001), the entire contents all of which are hereby incorporated by reference, involves an apparatus for electrical microcurrent stimulation therapy of a body part. This invention is intended to provide electrical microcurrent stimulation around an eye to combat visual system diseases such as age-related macular degeneration (AMD). The inventors claim that microcurrent stimulation will help rejuvenate the cells in the retina to slow or stop degeneration of the eye due to AMD. This invention does not involve any kind of a plate over the eyelid, nor does it involve heating. In a preferred embodiment, the electrical microcurrent is applied with a probe tip comprised of a cotton swab moistened or dampened with a conductive gel.

U.S. Pat. No. 7,069,084 (Yee, 2006), the entire contents all of which are hereby incorporated by reference, discloses a method for treating meibomianitis by massaging the muscle fibers in the eyelid that express the meibomian gland. The device is intended to cause the meibomian glands to expel any obstructing accreted meibum in the meibomian glands. According to the inventors, the obstructing plug may be composed of hardened lipids (as described above), cellular debris or some combination thereof. The invention involves the placement of electrical contacts on the eyelid and the application of an electrical current to the eyelids via the electrical contacts, which in turn induces muscular contractions within the eyelid. Unlike the present invention, this particular invention does not try to liquify or express accreted meibum from the internal Meibomian glands.

U.S. Pat. No. 7,122,013 (Liu, 2006), the entire contents all of which are hereby incorporated by reference, describes an eye massage device comprising a mask with left and right portions and left and right diaphragms in each eye portion. The mask is connected to a pneumatic-powered cylinder assembly via a plastic tube. The pneumatic-powered cylinder assembly comprises a cylinder that alternately delivers compressed air to the mask and draws air from the mask. In this manner, the eyes are massaged. In one embodiment, spacers are located between the diaphragms and the eyes as a means for absorbing tears secreted by the eyes during operation. This device is not handheld, and it does not provide heat to the eyelid.

U.S. Pat. No. 7,384,405 (Rhoades, 2008), the entire contents all of which are hereby incorporated by reference, involves a cosmetic instrument with a number of different interchangeable heads. These heads include abrasive attachments, oxygenating attachments, brush attachments, thermal attachments, and light radiating attachments. These various types of treatment attachments are moved over an area of skin and/or body part by the user manipulating the handle/Main Housing and also by a motion generator that moves the head portions. The motion generator may move the attachments by vibrating, spinning, oscillating, or propagating sonic waves through the head portions. The purpose of the thermal attachment is to facilitate the application of a cosmetic composition or solution onto the skin. The thermal attachment is moved over an area of skin or a body part in "upward circular or randomly directed strokes" until the composition or solution has been worked into, cleaned, and/or polished the skin or body part. This device is not specifically tailored to facilitate the application of a cosmetic composition or solution onto the skin of an eyelid disorder.

U.S. Pat. No. 7,637,878 (Lin, 2009), the entire contents all of which are hereby incorporated by reference, discloses an eye massaging device with built-in air pump and actuation elements, an inflatable fomentation member, and a belt member to which the main member and fomentation member are attached. The main member contains a number of slidably engaged pieces that elastically expand along with the belt member when the device is tied around a user's head. The fomentation member is shaped like an eyeshade and comprises a first outer piece, a second outer piece, an air bag and a thin heating element. The air pump and leakage valve inflate and deflate the air bag to press the warm heating element against the eyes with various levels of pressure. This device treats both eyes at once and would not be effective in treating a single eyelid.

U.S. Patent Application Pub. No. 2002/0156402 (Woog et al.), the entire contents all of which are hereby incorporated by reference, describes a device that applies sonic energy to various parts of the body for therapeutic purposes. The device comprises an applicator end at which a predetermined amplitude is generated under applied loads. This device does not involve massage of the eyelid.

U.S. Patent Application Pub. No. 2008/0200848 (Avni), the entire contents all of which are hereby incorporated by reference, involves a vibrating device that the inventor claims may be applied directly to a closed eyelid. This invention does not involve the application of heat to the eyelid, and the application does not include a single figure showing what the device would look like as applied to the eyelid.

None of the above inventions combine utilizing massage to effectively treat meibomian gland disease. What is needed is a handheld device that is easy to use, mechanically configured for placement over an eyelid, and that accomplishes massaging of the eyelid at the same time.

Accordingly, it is an object of the present invention to provide a handheld, battery-operated device with an oscillating, curved plate (for placement over the eyelid) that has a thermostatically controlled heating element within it. The oscillating motion of the curved plate applies a massaging action to the eyelid, and the heater is preferably controlled to achieve the optimum temperature. The present invention simultaneously liquefies and mobilizes the lipids in the meibomian glands, thereby causing them to move toward the gland orifices. With regular use, these oils remain less viscous, and the tear quality improves.

At least one eyelid cleaning device, the BlephEx® device described in US Published Patent Application Nos. 2014/0031845, 2014/0052164, and 2014/0214062, the entire contents all of which are hereby incorporated by reference, uses a design and unidirectional rotation virtually identical to that of ophthalmic burrs, but with a "sponge head" instead of a burr. Like ophthalmic burrs, the BlephEx® device drives a head with a full rotary motion and is for use by eyecare professionals. An "eyecare professional" is a person skilled in the art of ocular hygiene, such as ophthalmologists, optometrists, nurses trained in eyecare, and technicians trained in eyecare. The BlephEx® handpiece rotates a small sponge, is guided along the eyelid margin by an eyecare professional, removes scurf and debris, and exfoliates the eyelids. The key disadvantages of the BlephEx® device are its "motorized swab" design, unidirectional spinning (rotating) head (as distinct from an oscillating head moving in a reciprocally arcuate path), lack of instrumentation, and lack of safety features. Using an oscillating head to clean eyelids has significant advantages over existing art eyelid cleaning devices. Oscillating devices tend to be safer than rotary devices; an oscillating head does not have the directional "kick" (i.e., start-up torque) of a rotating head, so there is less chance of a user losing control of the device, e.g., the device jumping out of the user's hand. For that reason, devices with oscillating heads are easier to control than rotary devices. An oscillating eyelid care device does not induce a flinch response in the subject when the head first contacts an eyelid. An oscillating head creates fewer flying debris than a rotary head, making an oscillating head a better choice for work in an area where excessive flying debris might be a nuisance, such as near the eye.

The BlephEx® device can only safely be used by an eyecare professional due to the ergonomics and dynamics (e.g., "motorized swab" form, flinch induction, unidirectional rotation) of the device. The stick-like design (i.e., cylindrical handpiece with long, rotating, longitudinally aligned head) of the BlephEx® device, prevents the use of a BlephEx® device for SA Cleaning, i.e., for a patient to use in performing eyelid cleaning on him/herself. A device with a stick-like design must be used by a second person, typically by an eyecare professional.

Existing powered eyecare devices have heads with a constant unidirectional rotation, which require that the operator manually change the rotational direction (e.g., from clockwise to counterclockwise) of the head and retrace the path of cleaning to ensure efficient cleaning. An oscillating head provides better removal of debris and more uniform results than devices with unidirectional head rotation, which is the reason that oscillating heads are used in powered toothbrushes. The head of the driven attachment of a commercial, off-the-shelf powered toothbrush has a "brush head", and such driven attachment is called a "brush head attachment". Clinical studies in the dental care literature have shown that powered toothbrushes with an oscillating brush head are significantly better in reducing plaque and gingivitis compared to a manual toothbrush and brushing technique, and also compared to powered rotary toothbrushes. Just as the oscillatory movement of a powered toothbrush brush head ensures better cleaning than manual scrubbing, because a brush head typically oscillates at about 7,000 to 9,000 strokes/minute, the oscillatory movement of a powered handpiece coupled to an eyelid care module ensures better cleaning than manual scrubbing of the eyelids. The following publications, the entire contents all of which are hereby incorporated by reference, describes the comparative advantages of powered, oscillating head toothbrushes.

A comparative study of plaque removing efficiency using rotary electric and manual toothbrushes. Swed Dent J. 1991; 15:229-234. Cochrane Database Syst Rev. 2005; 18(2): CD002281.

J Am Dent Assoc. 2003 September; 134(9):1240-4. Manual versus powered toothbrushes: the Cochrane review.

Niederman R; ADA Council on Scientific Affairs; ADA Division of Science; Journal of the American Dental Association. Source:

DSM-Forsyth Center for Evidence-Based Dentistry, The Forsyth Institute, Boston, Mass. 02115, USA. rniederman@forsyth.org CONCLUSIONS: Powered toothbrushes with a rotation-oscillation action achieve a significant, but modest, reduction in plaque and gingivitis compared with manual toothbrushes.

National Institutes of Health Cochrane Database Syst Rev. 2005 Apr. 18; (2):CD002281. Manual versus powered toothbrushing for oral health.

Robinson P G, Deacon S A, Deery C, Heanue M, Walmsley A D, Worthington H V, Glenny A M, Shaw W C. Source: Department of Dental Public Health, School of Clinical Dentistry, University of Sheffield, Claremont.

Crescent, Sheffield, UK. peter.g.robinson@sheffield.ac.uk, CONCLUSIONS: Powered toothbrushes with a rotation oscillation action, reduce plaque and gingivitis more than manual tooth brushing.

Powered/electric toothbrushes compared to manual toothbrushes for maintaining oral health—Cochrane Report June 2014. Yaacob M, Worthington H V, Deacon S A, Deery C, Walmsley A, Robinson P G, Glenny A. This article reviews 56 studies published from 1964 to 2011 in which 5068 participants were randomized to receive either a powered toothbrush or a manual toothbrush. Majority of the studies included adults, and over 50% of the studies used a type of powered toothbrush that had an oscillation mode of action (where the brush head rotates in one direction and then the other, aka reciprocally arcuate). CONCLUSIONS: The evidence produced shows benefits in using a powered toothbrush when compared with a manual toothbrush. There was an 11% reduction in plaque at one to three months of use, and a 21% reduction in plaque when assessed after three months of use. For gingivitis, there was a 6% reduction at one to three months of use and an 11% reduction when assessed after three months of use.

One advantage of oscillating brush head powered toothbrushes, in general, is their ability to remove a greater amount of plaque in a given period of time than manual brushes. One study (Preber H, Swed. Dent. J. 1991; 15:229-234) found that 75% of dental biofilm was removed in 15 seconds with an oscillating powered toothbrush; the same amount of plaque removal required twice as long with a manual brush. The results of a more thorough cleaning process with oscillating powered toothbrushes can be extrapolated to eyelid hygiene using an oscillating powered device. However, powered toothbrushes cannot be easily adapted to eyelid care, given the large size of the handpiece, brush head attachment, and brush head, the stiff bristles on toothbrush brush heads (which would lacerate the eyelid margin, cornea, and sclera if used to clean eyelid margins), and the expense of disposable "necks" (the "neck" is the detachable distal portion of a powered toothbrush that terminates in a non-removable brush head, which means the entire neck must be discarded when the brush head wears, rather than disposal of only the brush head). Because powered toothbrush necks are not easily removed and are used for months before replacement, the brush heads become unsanitary. For sanitary eyelid care, the head of a device must be easily replaceable and inexpensive, or durable and autoclavable.

There is need for an eyelid care appliance that enables "self-administered cleaning" or "SA Cleaning".

Cleaning reduces risk of patient injury during training of eyelid care professionals, reduces risk of patient injury during SA Cleaning and SP Cleaning, provides an oscillating head, provides instrumentation and safety features that improve efficacy of eyelid care, provides an inexpensive and easily replaceable head (and alternatively, a durable and autoclavable head), and ideally provides an adjustable head angle and optionally provides control over oscillation frequency and angular sweep.

Recent research has concluded that meibomianitis is a condition that affects a vast number of individuals; some authors cite numbers as high as thirty percent of the population at fifty years of age. Researchers also agree that the condition becomes more common with age, which means that the percentages increase with an aging population. The disease is asymptomatic for some period of time—months to years—but almost always progresses. Eye physicians are well aware of this fact and the need to begin treatment as early as possible to alleviate damage from chronic disease. The very fact that the disease, in its early stages, is asymptomatic, coupled with the fact that treatments to date have their drawbacks or contraindications, leads doctors to allow the condition to go untreated until it becomes symptomatic and damage is done. In the later stages of the disease, treatment is more complex, costly and less-effective. The present invention will allow physicians to direct patients to a treatment method that is noninvasive, simple to use, and should provide years of service without ongoing expense.

The eyelid care appliance described and claimed herein solves the proceeding problems by providing, in a preferred embodiment, an oscillating, detachable sponge head, adjustable head angle, an ergonomic powered handpiece, sensors and other controls and instrumentation (such as, controls, indicators, displays, video, and/or data transmission), and auxiliary functions (cleanser, solvent, and medicament dispensing, gas and liquid dispensing, heating, and suction) that improve professional eyelid care, SA Cleaning, and SP Cleaning. The system utilizes cleansing action applied to the eyelids to effectively clean the eyelid and stimulate the meibomian glands.

In addition to meibomian gland dysfunction, other more acute eyelid conditions, which can occur at any age, are treated with warm massage. They too could be treated with the present invention; such common conditions as hordeolum and chalazion fall into this category.

In this application the use of daily disposable head means a soft-tip, spongehead, bristlebrush, Soft-Tip, bristlehead, sponge mount, sponge mount/head receiver interface or a round polymer head; all refer to the removable head of the device, and the terms are used interchangeably.

In this application the use of the singular includes the plural unless specifically stated otherwise and use of the terms "and" and "or" is equivalent to "and/or," also referred to as "non-exclusive or" unless otherwise indicated. Moreover, the use of the term "including," as well as other forms, such as "includes" and "included," should be considered non-exclusive. Also, terms such as "element" or "component" encompass both elements and components comprising one unit and elements and components that comprise more than one unit, unless specifically stated otherwise.

In this application the term silicon refers to a silicone or polysiloxane which can be any of a number of polymers that include any synthetic compound made up of repeating units of siloxane, which is a chain of alternating silicon atoms and oxygen atoms, combined with carbon, hydrogen, and sometimes other elements.

In the application the term silicone means any a soft elastomer, thermoplastic elastomer, silicone, mixture of silicone and thermoplastic elastomer In the application the term sponge means any medical-grade polyurethane foams or cellulose sponge which can include low-density polyether, polyvinyl alcohol ("PVA", which is highly absorbent), polyester (almost as absorbent as PVA, but more durable and has larger pores), and other polymers.

In this application the use of the term SA cleaning means "self-administered cleaning".

In this application the use of the SP cleaning means cleaning others' eyelids by a second party.

Numerical values for volumes and masses in this specification are shown in U.S. customary units. Teaspoons and tablespoons are taken as their volumetric equivalent units in the Avoirdupois system. Since accelerations and forces are not relevant to the description or use of the invention, U.S. customary units of weight such as ounces and pounds shall indicate their customary equivalent masses as stationary objects.

The present invention, the eyelid care appliance, is directed to novel devices and methods effective for restoring and maintaining good eyelid hygiene and capillary perfusion of the eyelids, lid margins and their adnexa, e.g. both prophylaxis and therapeutic treatment. The methods and devices disclosed herein include those for SA Cleaning and SP Cleaning, which enable better patient compliance with prescribed eyelid cleaning regimens, especially daily prophylaxis. The incidence of blepharitis increases as a function of age. If a person's neurological deterioration prevents them from performing SA Cleaning, a lay care-giver can perform SP Cleaning of such person's eyelids using the eyelid care appliance. These methods involve the easy and safe mechanical cleaning of an eyelid by eyecare professionals in clinical settings and by lay individuals in any location in which manipulation of the individual's eyelids or the eyelids of a second party is safe. "Second party" includes animals, especially household pets, horses, and farm animals. The present invention provides improved cleaning and capillary perfusion of the eyelid margins and meibomian gland orifices and enables a patient to clean his or her eyelids without assistance. The invention solves the technical problems of improved eyelid cleaning and training in eyelid cleaning, especially the technical problems in SA Cleaning and SP Cleaning. Devices such as those described in U.S. Patent Publication 2015/0182415 and U.S. Pat. No. 10,314,763 by Olkowski et al. are designed to clean the eyelid margins and meibomian gland orifices of cellular and sebaceous debris, the disclosure is hereby incorporated by reference in its entirety.

The key advantage of the instant invention is safe and effective daily use in the home performed by the patient or non-professionally trained.

Referring to FIG. 1a-d to FIG. 31, the invention will be more fully described.

Figure 20:
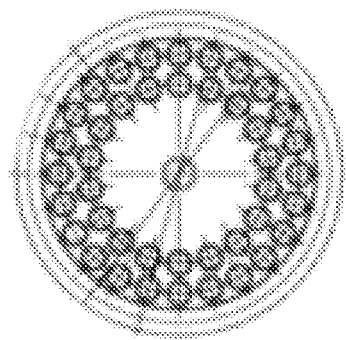
FIG. 20: is a Multiview drawing of the bristlebrush or Soft-Tip of the invention.
Figure 20:
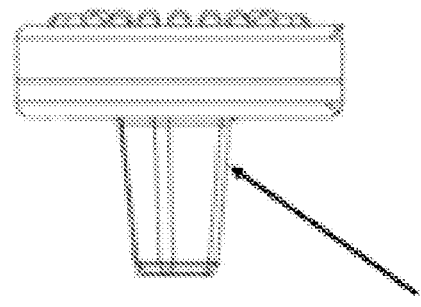
Figure 21:
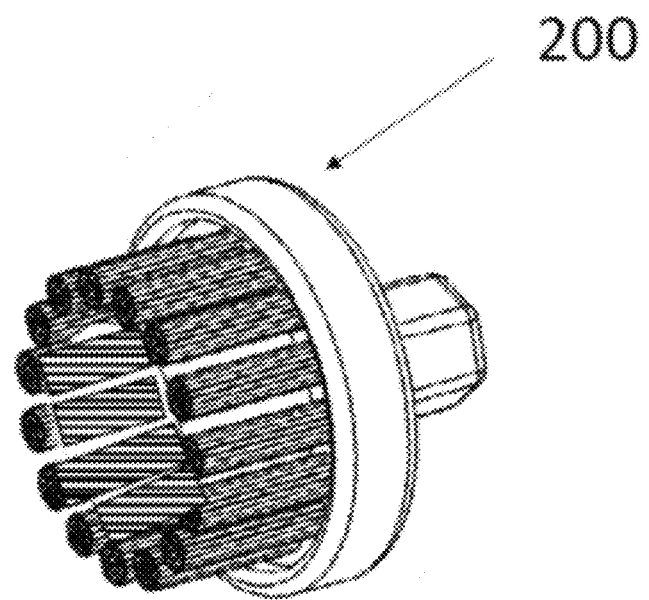
FIG. 21: is an alternative configuration of the bristlebrush or Soft-Tip of the invention.
Figure 23:
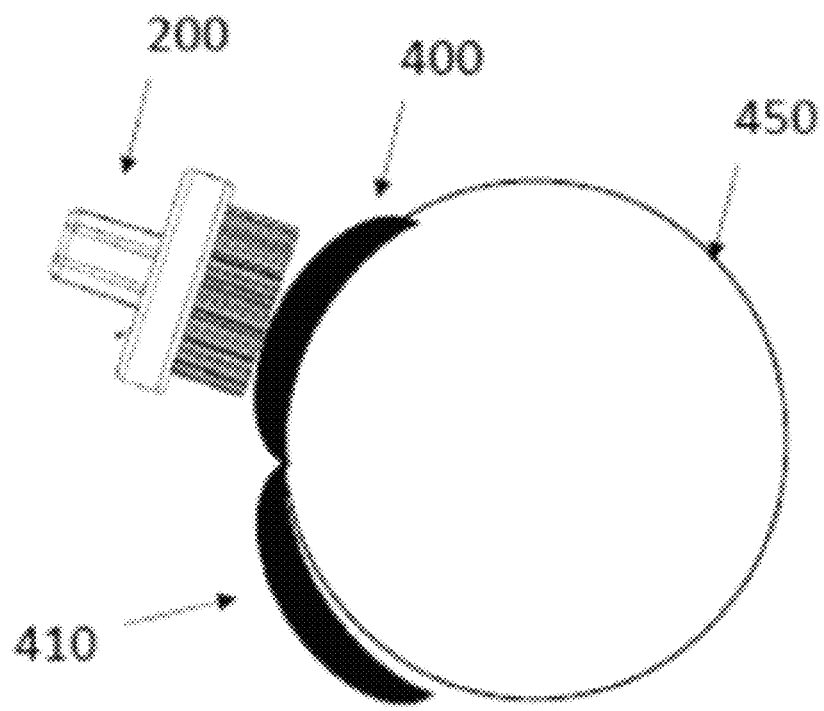
FIG. 23: illustrates how the bristlebrush or Soft-Tip is used to massage, and cleanse eyelids associated eye.

The application of the instant invention is shown in FIG. 23 which shows how the bristlebrush 200 or Soft-Tip 201 as shown in FIG. 20 and FIG. 21 is used to massage and cleanse eyelid and eyelash margins 400 and 410 which is associated eye 450.

As defined by the instant invention the term "head" means a soft-tip, spongehead, bristlebrush, Soft-Tip, bristlehead, sponge mount, sponge mount/head receiver interface or a round polymer head and all, refer to the removable head of the device unless otherwise denoted, and are fabricated from any combinations sponge, silicone and bristle head, or head made with materials other than sponge and bristles such as a soft elastomer, thermoplastic elastomer, silicone, mixture of silicone and thermoplastic elastomer. The motive action of the driving means is transmitted through from the motor through the drive system to the head receiver. The eyelid care appliance is always used with a cleanser and/or lubricant that is applied to the head and/or directly to the eyelids being cleaned. In addition to cleanser and/or lubricants, medicaments can be applied to the head and/or directly to the eyelids being cleaned. When a user turns on an eyelid care appliance, and applies the oscillating head to an eyelid, oscillation of the head cleans, massages, and stimulates the eyelash margins, eyelid margins and meibomian gland orifices of cellular and sebaceous debris. Such cleaning prevents, for an ensuing period, gland obstruction and promotes health of the glands in the eyelid. The oscillation frequency and angular sweep can optionally be user-selected and implement via printed circuit board 11, control of motor 7. Oscillation frequency of the head is nominally 7,000 to 9,000 strokes/minute and angular sweep of the head is nominally 70 degrees (i.e. the head travels 70 degrees forward followed by 70 degrees backwards). Higher frequency pulsation (nominally 20,000 to 40,000 pulses/min.) can optionally be generated by the motor 7 and fed to the head receiver 6. The ability to achieve cleaning of the patients meibomian gland orifices by applying the oscillating head to the eyelid, improves the patient cleaning experience of the eyelid margin.

The vibration and/or sonic action of the disposable tip, facilitates stimulation of the Meibomian glands and capillary perfusion as previously described.

The vibration and/or sonic action facilitates use of the device over a closed eyelid and, therefore, in closer proximity to long axis of the Meibomian glands, thereby increasing the energy delivered to the entire length of the Meibomian glands. Compared to the direct method, applying the disposable tip to the eyelid margin, in which the energy is transmitted primarily to the openings of the Meibomian glands, this indirect method facilitates additional therapeutic effects by primarily delivering energy to the long axis of the Meibomian glands which can extend 4-5 mm into the body of the eyelid.

An additional use for the instant invention when the indirect method is used, for stimulation is improving capillary perfusion and cleaning the eyelash margins. Many patients suffer from blepharitis. Used in this fashion the instant invention has a greater therapeutic effect on the follicles of the lashes, promoting greater length and thickness of the eyelashes, while diminishing debris and parasites such as the Demodex mite.

Another embodiment of the device utilizes a piezo electric mechanism to create the therapeutic effect. The frequency of the piezo electric mechanism adds an ultrasound dimension to the treatment effect.

The soundwaves generated by the piezo electric mechanism and delivered by the disposable tip, penetrate the eyelids vibrating the Meibomian glands, creating an effect similar to lithotripsy, which contributes to breaking up the accreted meibum in the glands, facilitating the expulsion of the accretions.

A basic embodiment of the invention comprises a power supply (e.g. battery), drive module that causes oscillation of a head receiver, detachable head mounted in the head receiver, drive control, and a housing that contains the preceding elements. The housing has a proximal portion, preferably ergonomic, that is easily gripped by hand. The proximal portion of the housing in this embodiment also contains drive control (at least on/off, and optionally status LED(s), oscillation frequency, oscillation sweep angle, and timer). A status LED 207 can indicate simply power on (if lit), or one or more LEDs can additionally indicate battery charge level, head oscillation frequency, and other operational states.

The instant invention can also utilize the LED system for LED light therapy. The preferred therapy color is Red, as Blue decreases oil gland production. However, other LED light colors have been found to be beneficial. Red light therapy is commonly referred to as photo-biomodulation (PBM), low level light therapy (LLLT), soft laser therapy, cold laser therapy, biostimulation, photonic stimulation, low-power laser therapy (LPLT).

The theory behind Red light therapy is that the red light produces a biochemical effect in cells that strengthens the mitochondria. The mitochondria are the powerhouse of the cell—it's where the cell's energy is created. The energy-carrying molecule found in the cells of all living things is called ATP (adenosine triphosphate). Additionally, Red, or infrared, light is used for treating the epidermis, which is the outer layer of skin. When the light is applied to your skin, the epidermis absorbs it and then stimulates collagen proteins.

Figure 18C:
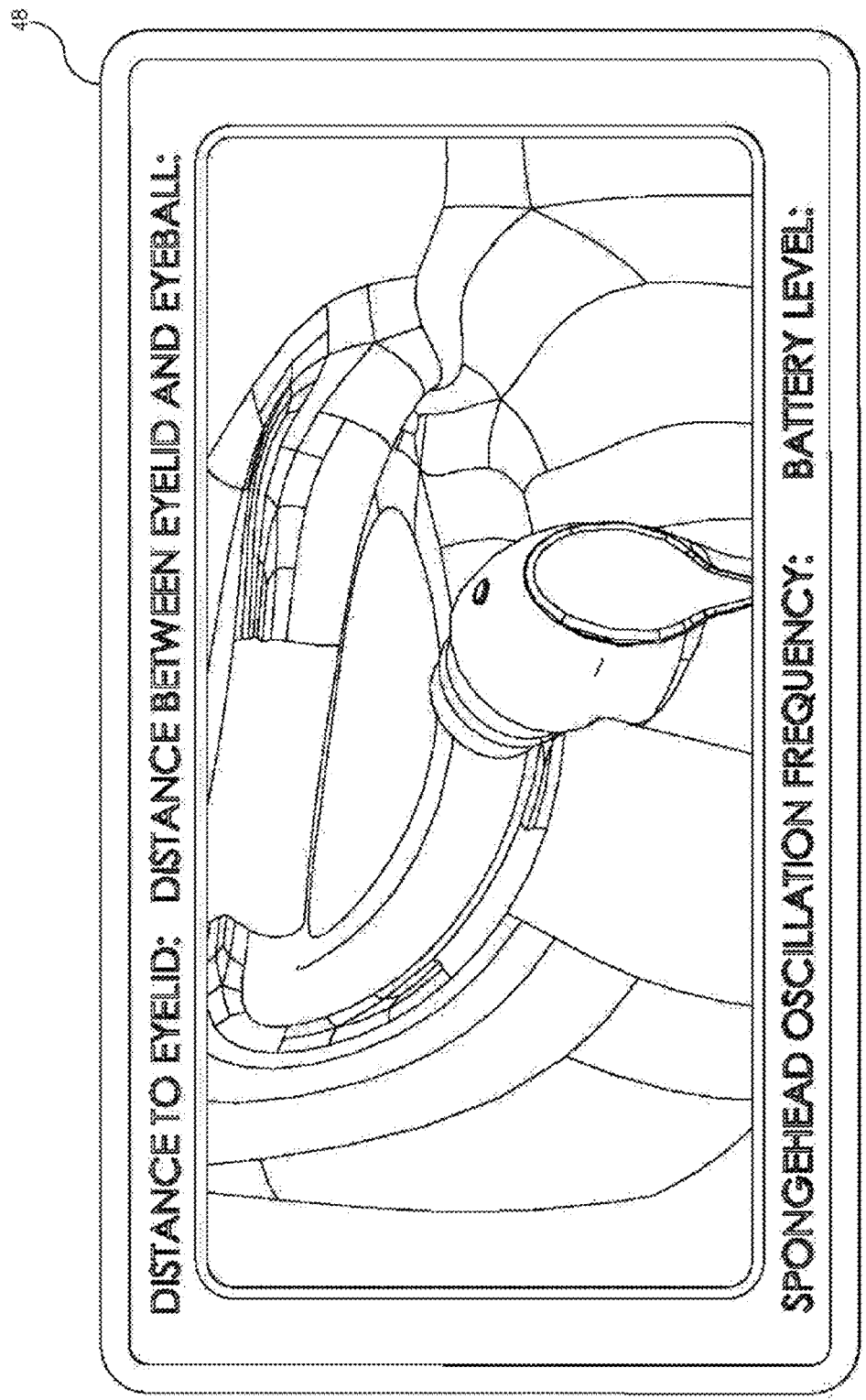
FIG. 18c: Smart Device Display Showing Video from Eyelid Care Appliance Provided by Video Proximity System via Near Field Communication Channel.

In theory, more collagen means that your skin will look smoother and fuller, which can reduce the appearance of fine lines and wrinkles. Red LED light is also thought to reduce inflammation while improving circulation, which can give you a healthier glow. A more detailed discussion can be found in https://www.healthline.com/health/red-light-therapy#how-does-it-work? and https://www.healthline.com/health/beaty-skin-care/led-light-therapy A preferred embodiment of the invention comprises a power supply (e.g., battery), drive module that causes oscillation of a head receiver, detachable head mounted in the head receiver, drive control and annunciator, proximity system, and a housing that contains the preceding elements. The housing has a proximal portion, preferably ergonomic, that is easily gripped by hand. The proximal portion of the housing in this embodiment also contains drive control (described above) and proximity control and annunciator. The details of the proximity system, control, and annunciator depend upon the configuration of the proximity system. In a video proximity system, the control is at least on/off (and optionally typical video controls, such as manual or auto iris, and gain) and the annunciator is preferably a mobile display linked to the video camera by NFC. In this embodiment, proximity system control is preferably performed through one or more software applications ("smart apps") running on the smart device, and would enable recording video of the eyelid cleaning in the memory of the smart device or of the eyelid care appliance. Proximity system settings performed by smart apps or by applications running on the printed circuit board 11 can include the generation of audible tones that reflect distance between the head and the closest surface and optionally the second closest surface to the head (typically the eyelid margin is closest and the cornea or sclera is second closest surface), colors or icons on the smart device display that indicate distance, or the generation of a glideslope display on the smart device that guides a user in landing the head on an eyelid margin; preferably, one or more lights (e.g., LEDs) on the housing project light in front of the head in video-equipped embodiments of the invention. The output of the proximity system software can include the distance between head and eyelid, the distance between eyelid and eyeball, the battery level, the head oscillation frequency, and other data to assist the user; such output can be displayed on the smart device, as shown in FIG. 18*c*. The proximity system can evaluate or score user performance as if the use of the eyelid care appliance were a video game. This embodiment is called the "simple proximity embodiment" of the invention. Alternative embodiments include a video display (typically, a LCD) mounted on or integral with the eyelid care appliance, projected video, or a video goggle. A video-based proximity system also provides magnification of the treated area and documentation of the progress, and thus makes it easier to learn to use the eyelid care appliance, and to visually confirm cleanliness of treatment area.

A further development of the device includes a touch pad and/or activator switch built into the base of the device. Many dry eye disease sufferers are elderly and their hands and fingers may be affected by arthritis and or reduced dexterity. By placing the activator switch or touch pad in the base of the instrument, the instrument can be turned on/off, and operation modes can be changed by grasping the instrument and depressing the base on a hard surface, such as a countertop. When a touchpad is used, simply touching the base of the instrument with the hand/fingers will facilitate operation.

A "bristlehead or Soft-Tip" is preferred for eyelid care, but other materials and configurations of heads can be used in the invention, particularly for treating areas other than eyelid margins. A spongehead is an alternative configuration and it means a synthetic sponge in a disc, cylindrical, globular, and other shape that is adhered to a "sponge mount". A head of the invention comprises (i) a bristlehead or Soft-Tip mount with a male or female portion (preferably a male mating portion, such as a post) that mates with a "head receiver" (preferably with a female mating portion, such as a socket) and (ii) a bristlehead or Soft-Tip (or other material adapted for cleaning the eyelid or other areas), selected for use for cleaning a target surface, such as the eyelid. Key selection factors for the bristlehead or Soft-Tip are surface topology, elasticity, shape memory, degree of smoothness, level of porosity, and hydrophilic nature of the head. Material selection determines whether the head is inexpensive, or durable and autoclavable.

Figure 8C:
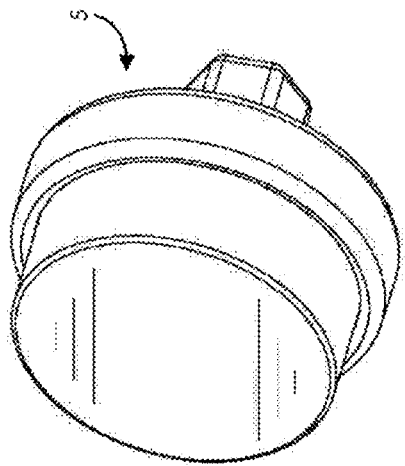
FIG. 8*c*: Cylindrical Head Isometric View
Figure 8B:
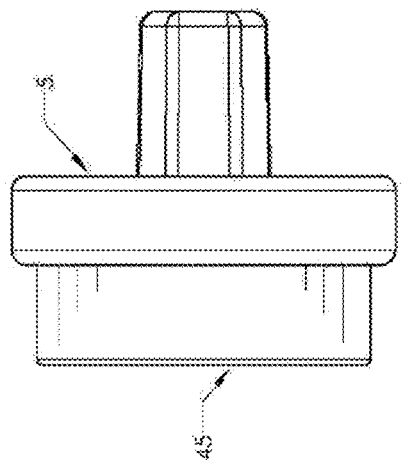
FIG. 8*b*: Cylindrical Head Side View
Figure 8A:
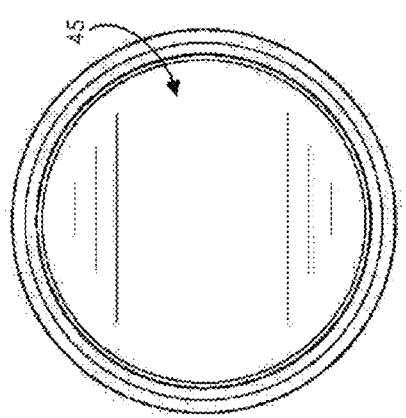
FIG. 8*a*: Cylindrical Head Front View

The instant invention can be used with any head configuration including bristlehead or Soft-Tip, spongehead, round polymer head, as shown in FIGS. 8*a-c,* 9*a-c,* 10*a-c* and 11*a-c.*

A head mount mates with a head receiver that is connected to and driven by the drive system so that the head mated with the head receiver oscillates when the motor is powered on. Friction between the post and socket in the sponge mount/head receiver interface are typically more than adequate to keep the head firmly affixed to the head receiver, but still removable for replacement of the head. Alternatively, a weak adhesive can be applied, or a physical detent used in the plug and socket, to more firmly retain the head in the head receiver, yet permit removal of the head without tools. The sponge mount and head receiver are typically made of a plastic selected to withstand rapid oscillation and devoid of small cavities that can be colonized by bacteria. A post can have any shape that prevents rotation or slippage of the sponge mount when the sponge mount is mated with the head receiver. In addition, a permanent magnet or electromagnet mounted inside the chuck, "pulls" the sterile tip into place by means of a steel rod inside the shaft of each soft-tip. The post shape is preferably a polygonal shape, such as a hexagon, triangle, rectangle, or star-shape.

The sponge material, porosity, shape, and other parameters are selected based on treatment objectives, e.g., maintaining eyelid health, treating eyelid conditions and diseases, dermabrasion, polishing, etc.

Sponge materials may be low-density polyether, polyvinyl alcohol ("PVA", which is highly absorbent), polyester (almost as absorbent as PVA, but more durable and has larger pores), and other polymers. A head can have various surface textures, topologies, porosities, permeabilities, dimensions, inlet (e.g., suction) channels, and outlet (e.g., dispensing) channels. The bristlehead or Soft-Tip can be pre-impregnated with topical pharmacologic or cleansing agents to better facilitate application and efficacy of the agents. Alternatively, topical agents can be applied to the daily disposable soft-tip, bristlebrush, or Soft-Tip before applying the head to an eyelid or can be applied using a reservoir-equipped embodiment of the invention.

Other embodiments of the daily disposable soft-tip include forming the disposable from plant starch and/or gelatin, that retains the favorable characteristics of pliability, softness, and smoothness, yet erodes or "melts" as the disposable comes into contact with either or both the lubricant and/or the patient's tears. As the tip melts, active ingredients disperse evenly throughout the matrix; anti-infectives, anti-inflammatory agents, and analgesics are released in a controlled fashion, thus causing the active ingredient to be released at a desired rate throughout the duration of the nanomites. This provides a programmed release based on duration of mechanical, chemical, or electrical effect which are mixed into the tip matrix (and therefore held in a non-oxygenated state), thus preserving their designed treatment effect for an extended period of time.

Typical anti-inflammatory agents can be added to the tip matrix either individually or in combination and are selected from the group including aspirin, acetylsalicylic acid, salicylic acid, celecoxib (Celebrex), diclofenac (Cambia, Cataflam, Voltaren-XR, Zipsor, Zorvolex), diflunisal (Dolobid—discontinued brand), etodolac (Lodine), ibuprofen (Motrin, Advil), Ketorolac tromethamine, indomethacin (Indocin) and drugs that meet the definition of NSAIDs—nonsteroidal anti-inflammatory drugs. The anti-inflammatory agent has to be mixed by high energy sonification to form a suspension with the selected oil. The oils can be selected from various oils which will mix with the RTV silicone rubber (room-temperature-vulcanizing silicone), which include flax seed oil, silicone oil, cannabidiol (CBD oil), olive oil, peanut oil and other natural oils. Silicone oils are any liquid polymerized siloxane with organic side chains. The silicone is used to mean any soft elastomer, thermoplastic elastomer, silicone, mixture of silicone and thermoplastic elastomer.

Figure 29:
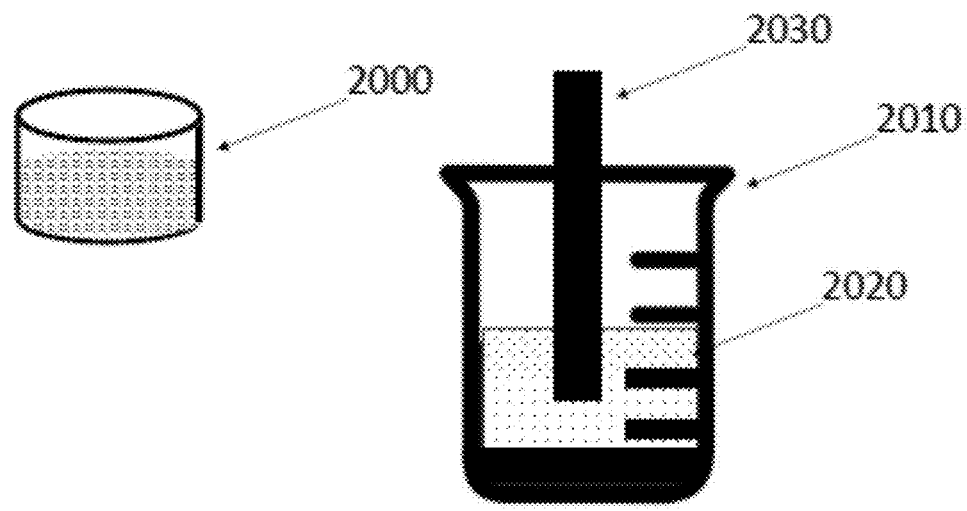
FIG. 29: shows forming a mixture of an anti-inflammatory agent in flax seed oil.

First, an anti-inflammatory agent and oil mixture must be created to suspend the anti-inflammatory agent in the oil. The anti-inflammatory agent as shown in FIG. 29 is created by sonicating the anti-inflammatory agent in the flax seed oil. An example of a typical preparation of the mixture is to take the 10 mg of Sigma A5376 acetylsalicylic acid powder 2000 and placing it in a 300-ml suitable glass container such as a beaker 2010. Then add 200 ml of flax seed oil 2020 but any oil described can be used. The anti-inflammatory agent has to be mixed by high energy sonification to form a suspension with the selected oil. To accomplish mixing, the next step is to place the sonicator tip 2030 of a Branson Sonifier 450 so that it extends to approximately 2 mm from the bottom of the beaker. Set the power supply for controls accordingly, to 20% Duty Cycle, output control to 6 and timer to 8. Cover the beaker with a piece of plastic film such as Parafilm® M Sealing Film to prevent splatter or contamination and sonicate for 20 minutes. The sonification can also be completed in other devices such as placing the glass container in a Branson HT50 ultrasonic bath cleaner and sonicating the mixture until all the powder of the anti-inflammatory agent is suspended in the flax seed oil. One should note that the container should not come in contact with the bottom of Branson HT50 ultrasonic bath cleaner.

To create an anti-inflammatory agent bristlebrush or Soft-Tip 200 utilizing aspirin, acetylsalicylic acid and oil mixture, one would add the anti-inflammatory agent and oil mixture into the silicon at a concentration of 0.5-8 mg/ml. The following process is used: take the appropriate amount of the acetylsalicylic acid and oil mixture needed to arrive at a 0.5-8 mg/ml mixture of anti-inflammatory agent and silicone (the preferred concentration is 2.5 mg/ml), and add it to the silicone mixing it completely. Then utilize the mixture to mold the bristlebrush or Soft-Tip 200, followed by curing the bristlebrush or Soft-Tip 200 in an oven which is heated to 200 degrees C., and allow the bristlebrush or Soft-Tip 200 to cure for 4 hours or until the bristlebrush or Soft-Tip 200 is firm yet supple.

The addition of acetylsalicylic acid into the matrix result in a bristlebrush or Soft-Tip 200 that has anti-inflammatory properties which will minimize the problems of inflammation which could affect the eye heath of the patient. The bristlebrush or Soft-Tip 200 is utilized by the patient applying the oscillating bristlebrush or Soft-Tip 200 on the distal end of the appliance to the eyelid, to scrub the eyelid and the meibomian glands on the edge of the eyelid.

Anti-infectives describe any medicine that is capable of inhibiting the spread of an infectious organism or by killing the infectious organism outright. This term encompasses antibiotics, antifungals, anthelmintics, antimalarials, antiprotozoals, antituberculosis agents, and antivirals. Typical anti-infective agents can be added to the tip matrix either individually or in combination, and can be selected from the group including:

Curcumin;
Silver;
Copper;
Amebicides;
Aminoglycosides;
Azole antifungals;
Echinocandins;
Polyenes;
Antiviral agents;

Aminoglycosides are a class of antibiotics used mainly in the treatment of aerobic gram-negative *bacilli* infections, although they are also effective against other bacteria including *Staphylococci* and *Mycobacterium tuberculosis*. They are often used in combination with other antibiotics. Typical aminoglycosides agents can be added to the tip matrix either individually or in combination, and can be selected from the group including paromomycin, tobramycin, gentamicin, paromomycin sulfate, amikacin, amikacin liposome, kanamycin, neomycin and plazomicin.

Figure 30:
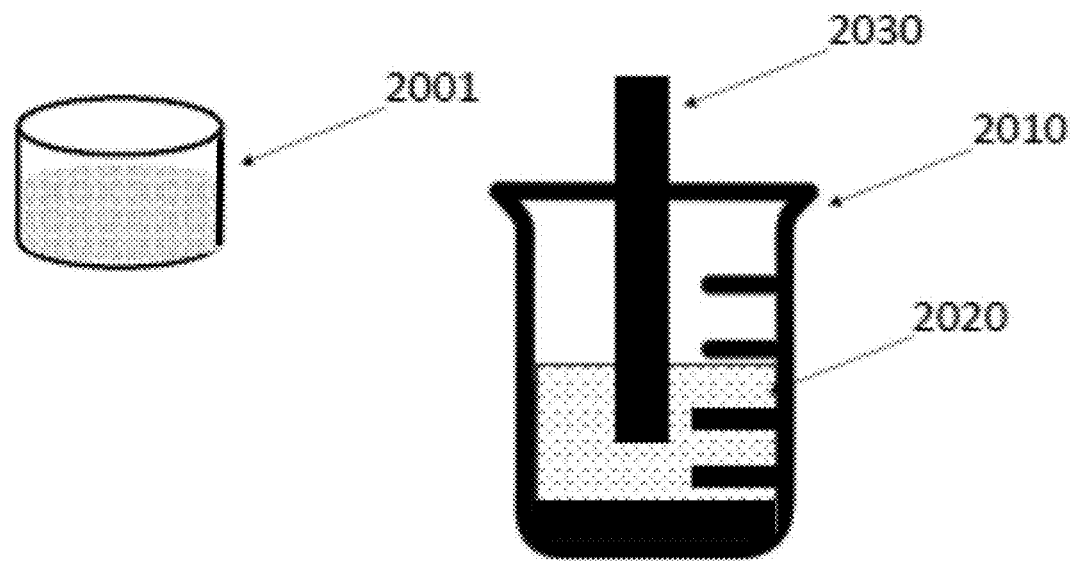
FIG. 30: shows forming a mixture of an aminoglycosides agent in flax seed oil.
Figure 31:
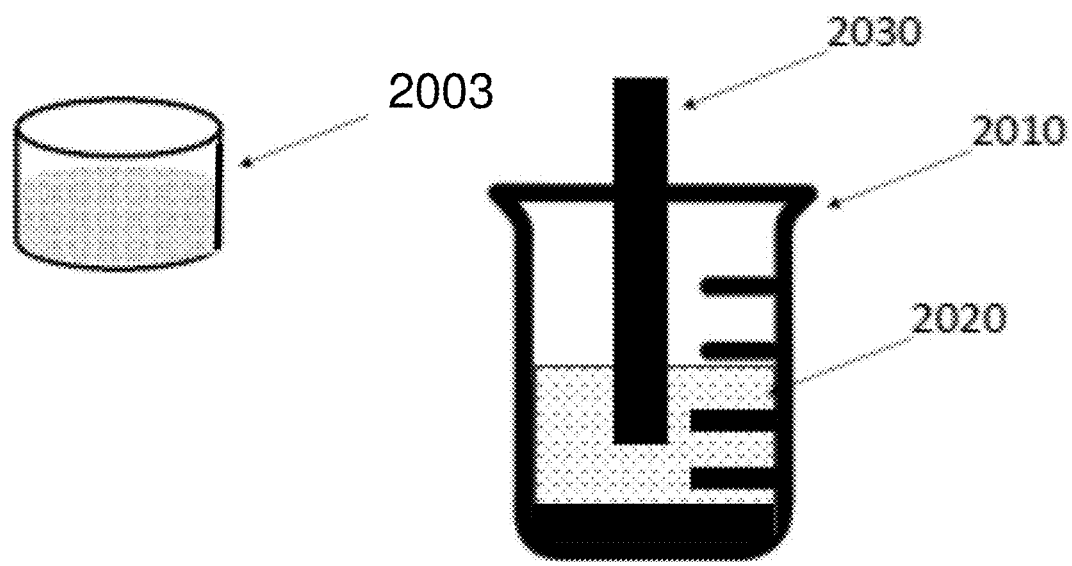
FIG. 31: shows forming a mixture of curcumin in flax seed oil.

To create an anti-infective bristlebrush or Soft-Tip 200 using an aminoglycosides agent one must create an aminoglycosides agent and oil mixture. The aminoglycosides agent as shown in FIG. 30 is created by sonicating the anti-inflammatory agent in the flax seed oil. An example of a typical preparation of the mixture is to take the 15 mg of paromomycin sulfate 2001 from sigma Aldrich part number 15000003 and placing it in a 300-ml suitable glass container such as a beaker 2010. Then add 200 ml of flax seed oil 2020, but any oil described can be used. Then place the sonicator tip 2030 of a Branson Sonifier 450 so that it extends to approximately 2 mm from the bottom of the beaker. Set the power supply for controls accordingly to 20% Duty Cycle, output control to 6 and timer to 8. Cover the beaker with a piece of plastic film such as Parafilm® M Sealing Film to prevent splatter or contamination and sonicate for 20 minutes. The sonification can also be completed in other devices such as placing the glass container in a Branson HT50 ultrasonic bath cleaner and sonicating the mixture until all the powder of the of paromomycin sulfate 2001 is suspended in the flax seed oil. One should note that the container should not come in contact with the bottom of Branson HT50 ultrasonic bath cleaner.

To create an anti-infective bristlebrush or Soft-Tip 200 utilizing an aminoglycosides agent such as paromomycin and oil mixture, one would add the paromomycin and oil mixture into the silicone at a concentration of 0.4-9 mg/ml. The following process is used: take the appropriate amount of the paromomycin and oil mixture needed to arrive at a 0.4-9 mg/ml mixture of paromomycin and silicone (the preferred concentration is 3 mg/ml), and add it to the silicone mixing completely. Then utilize the mixture to mold the bristlebrush or Soft-Tip 200, followed by curing the bristlebrush or Soft-Tip 200 in an oven heated to 200 degrees C., and allow the bristlebrush or Soft-Tip 200 to cure for 4 hours or until the bristlebrush or Soft-Tip 200 is firm yet supple.

The addition of paromomycin into the matrix, results in a bristlebrush or Soft-Tip 200 that has anti-infective properties which will minimize the problems of inflammation, which could affect the eye heath of the patient. The bristlebrush or Soft-Tip 200 is utilized by the patient applying the oscillating bristlebrush or Soft-Tip 200 on the distal end of the appliance to the eyelid to scrub the eyelid and the meibomian glands on the edge of the eyelid.

To create an anti-infective bristlebrush or Soft-Tip 200 using a natural product such as curcumin, one must create a curcumin and oil mixture. The curcumin and oil mixture as shown in FIG. 31 is created by sonicating the curcumin in the flax seed oil. An example of a typical preparation of the mixture is to take the 10 mg of curcumin powder 2003 from sigma Aldrich part number C1386-10G and place it in a 300-ml suitable glass container such as a beaker 2010. Then add 200 ml of flax seed oil 2020, but any oil described can be used. Then place the sonicator tip 2030 of a Branson Sonifier 450 so that it extends to approximately 2 mm from the bottom of the beaker. Set the power supply for controls accordingly to 20% Duty Cycle, output control to 5 and timer to 7. Cover the beaker with a piece of plastic film such as Parafilm® M Sealing Film to prevent splatter or contamination, and sonicate for 15 minutes. The sonification can also be completed in other devices such as placing the glass container in a Branson HT50 ultrasonic bath cleaner and sonicating the mixture until all the curcumin powder 2003 is suspended in the flax seed oil. One should note that the container should not come in contact with the bottom of Branson HT50 ultrasonic bath cleaner.

To create an anti-infective bristlebrush or Soft-Tip 200 utilizing curcumin and oil mixture, one would add the curcumin and oil mixture into the silicon at a concentration of 0.4-9 mg/ml. The following process is used: take the appropriate amount of the curcumin and oil mixture needed to arrive at a 0.4-9 mg/ml mixture of curcumin and silicone (the preferred concentration is 4 mg/ml), and add it to the silicone mixing completely. Then utilize the mixture to mold the bristlebrush or Soft-Tip 200, followed by curing the bristlebrush or Soft-Tip 200 in an oven which is heated to 200 degrees C., and allow the bristlebrush or Soft-Tip 200 to cure for 4 hours or until the bristlebrush or Soft-Tip 200 is firm yet supple.

The addition of curcumin into the matrix result in a bristlebrush or Soft-Tip 200 that has anti-infective properties which will minimize the problems of infection which could affect the eye heath of the patient. The bristlebrush or Soft-Tip 200 is utilized by the patient applying the oscillating bristlebrush or Soft-Tip 200 on the distal end of the appliance on the eyelid to scrub the eyelid and the meibomian glands on the edge of the eyelid.

Another method of making a head with anti-infective and anti-inflammatory properties the flax seed oil is prepared with tea tree oil in a concentration of 5% -50%. First tea tree oil is placed in a beaker of 200 ml of flax seed oil and ultrasonically mixed until the tea tree oil is mixed into the flax seed oil and the flax seed oil and tea tree oil mixture is then added to silicon and/or thermoplastic elastomer such that the concentration of flax seed oil and tea tree oil to silicon and/or thermoplastic elastomer for the silicon and/or thermoplastic elastomer mixture is 3 mg/ml and flax seed oil and tea tree oil silicon and/or thermoplastic elastomer mixture is molded into a head and cured for 4 hours at 200 degrees C.

A method of making a head with anti-infective and anti-inflammatory properties where in hypochlorous acid 0.01% is placed in a beaker of 200 ml of flax seed oil and ultrasonically mixed until the hypochlorous acid is mixed into the flax seed oil and the flax seed oil and the hypochlorous acid mixture is then added to silicon and/or thermoplastic elastomer such that the concentration of flax seed oil and hypochlorous acid to silicon and/or thermoplastic elastomer for the silicon and/or thermoplastic elastomer mixture is 3 mg/ml and the flax seed oil and hypochlorous acid silicon and/or thermoplastic elastomer mixture is molded into the head and cured for 4 hours at 200 degrees C.

The head used in the invention is preferably sterile and can be easily replaced. The head is sterilized and distributed to users in packaging that maintain sterility. Sterility is desired since a head is used to clean eyelids and in close proximity to the cornea and other exposed parts of the eye, and in other embodiments is used in debridement and wound treatment. A magnetic chuck could be used to grasp and hold the head to the drive mechanism of the instant invention. Another embodiment affixes the steel pin permanently to the chuck of the hand-held device. A head can be easily replaced by pulling it off the head receiver. Periodic replacement of a disposable head is typically daily in a home use setting (i.e., for SA Cleaning), or for each patient in a clinical setting.

Alternative embodiments of the instant invention comprise one or more of the following elements: (i) illumination source(s) with on/off and optionally with light intensity control, (ii) one or more refillable reservoirs, pumps, and outlet channels for solvent, cleanser, medicament, and other liquids, powders, and gases (the gases may be heated, cooled, or room temperature and may be used to create an aerosol from a liquid or powder), (iii) means of metering and application of liquids, powders (and other solids), and gases, (iv) a suction pump that creates suction in or near the head to remove debris, cleanser, and other matter from a surface being cleaned or treated, (v) sensors and optionally processors to assay the distance from head to target area, materials in target area, and/or materials in suction waste stream, (vi) indicators (visual and aural) and displays, (vii) video camera, and data communication channels (wired and/or wireless). The hardware and software used to perform an assay may be located in the handpiece or located remotely and linked with the eyelid care appliance by NFC. A head can also comprise bristles, typically very small diameter bristles, alone or in combination with a sponge. In some head embodiments, the bristles terminate very close to the surface of a head. Refilling a reservoir is performed by connecting a liquid, gas, or powder source to an inlet connector on the housing in communication with the reservoir. Alternatively, a reservoir can be removed from the housing for refilling. An eyelid care appliance can comprise one or more reservoirs, reservoir inlet connectors, pumps, output tubing, and nozzles for dispensing solvent, cleanser, medicament, and other liquids, powders, and gases. Configurations with two reservoirs, associated pumps and tubing can be filled with agents that create heat when combined. When such agents are dispensed and combine on the eyelid surface, the eyelid surface is heated, thereby helping to "melt" blockages of meibomian glands posterior to the anterior surface or an eyelid.

Alternatively, to heat the head an electric current can be routed through the tip, so as to allow the system to heat in tip, by using conductive material/wires in the tips.

A preferred embodiment further comprises one or more reservoirs, reservoir inlet connectors, pumps, output tubing, and nozzles for dispensing liquids selected from the group comprising cleaning agents, Betadine, antiseptics, antimicrobials, anti-inflammatories, anesthetics, saline solution, water, solvents, taggants, stains, pharmaceuticals, nutraceuticals, and monoclonal antibodies. Another preferred embodiment further comprises one or more reservoirs, reservoir inlet connectors, housing inlets, pumps, output tubing, and nozzles for dispensing gases, wherein optionally the gases are heated or cooled by a thermal device in the output tubing can optionally be used to create an aerosol from a liquid or powder sourced from a different reservoir, and can optionally be used to create an aerosol from a liquid or powder each stored in a different reservoir. The gas can be ambient air fed to the pump from an inlet in the housing rather than from a reservoir.

The preferred embodiment is an "integral" eyelid care appliance in which all elements of a given configuration are contained in a single housing. A drive module (defined below) and an eyelid care module (defined below) are the principal elements contained in the housing. A preferred embodiment comprises a power supply, motor, drive system that transmits motive force from the motor to oscillate a head receiver, motor controls, a proximity system, and proximity annunciator contained in a housing, wherein a head is detachably mated with the head receiver and protrudes from the housing and oscillates when the motor is powered on. An alternate "two-piece" embodiment comprises a handpiece and a detachable neck, a power supply, motor, proximity annunciator, and motor control being contained in the handpiece, a head receiver being contained in the detachable neck and connected to the motor through a drive system with portions of the drive system distributed in the detachable neck and in the handpiece, and with a coupler at the interface of the handpiece and detachable neck, which drive system transmits motive force from the motor to oscillate the head receiver, wherein a head is detachably mated with the head receiver, protrudes from the detachable neck, and oscillates when the motor is powered on. In a two-piece embodiment, each of the components recited in items (i) to (vii) above can be distributed in whole or in part, between the handpiece and the detachable neck, depending upon the component and configuration involved. In two-piece embodiments of the invention, the detachable neck comprises an eyelid care module, the neck is detachably mated with a handpiece containing a drive module and the interface between the detachable neck and the handpiece includes a drive system interface (e.g., a mechanical coupling such as a male shaft mating with a female receiver, wherein the shaft and receiver have mating geometries, such as a D-shape, triangle shape, star shape, etc., or a magnetic coupling).

In all embodiments of the invention, a power supply (typically a replaceable and/or rechargeable battery) powers a DC motor, and when the motor is powered on, the motor (and drive translator, if the motor outputs unidirectional rotary motion) causes the oscillation of a driveshaft (or equivalent means of transmitting motive force, e.g., in a two-piece embodiment, an electric motor with magnetic or mechanical coupling to a detachable neck). The oscillating driveshaft causes the head receiver to oscillate, which causes the head mounted in the head receiver to oscillate. The eyelid care appliance is typically battery powered; however, it can be powered by a power supply connected to an electrical outlet.

A "drive module" comprises a power supply, motor, on/off control, drive shaft, and related transmission elements. If the motor outputs unidirectional rotary motion, such unidirectional rotary motion is translated so that the driveshaft causes the head to oscillate. The combination of the motor, driveshaft, and related transmission elements (such as a drive translator) is called a "drive system". A well-known drive translator has a motor-driven driveshaft with pinion gear driving a geared disc or cam. An eccentric follower link on the geared disc or cam causes a shaft linked to the geared disc or cam to oscillate. The drive system couples the motive force of the motor to the head.

An "eyelid care module" comprises at least a head, head receiver, and associated drive system. Integral and two-piece embodiments of the invention can be configured to provide the same functionality. However, functionality of two-piece embodiments may be limited by the functionality of the handpiece. For instance, a detachable neck (containing an eyelid care module) that mates with a generic powered handpiece, e.g. an electric toothbrush handpiece, would have to have additional functionality configured in the detachable neck.

As shown in FIGS. 1a to 1d, and 2a to 2c, a basic embodiment of the invention comprises a drive module and an eyelid care module in a single, "integral" housing 1. A bristlebrush or Soft-Tip 200 comprising a mount 5 which is mounted on the distal end of the appliance or device.

In embodiments in which the head angle (the angle between the axis of oscillation of the bristlebrush or Soft-Tip 200 and the longitudinal axis of the housing 1) is non-adjustable, the head angle is fixed between zero and 90 degrees. In embodiments in which the head angle is adjustable (see FIG. 19), the head receiver pivots in a frame that either has detents at given head angles (e.g., 30 degrees, 45 degrees, 60 degrees, etc.) or has a locking mechanism that holds the head at a user selectable head angle. The head can also be locked in place at each detent position. The preferable head angle is typically in the range from 20 degrees to 80 degrees, and preferably in the range of 45 to 65 degrees. The primary factor in selecting the head angle is to facilitate SA Cleaning and to accommodate user comfort in holding and manipulating the eyelid care appliance. Both integral and two-piece embodiments of the invention can have a head receiver with adjustable head angle ("adjustable head receiver"). Embodiments of the eyelid care attachment with adjustable head receivers can use a ball joint, U-joint, or geared joint as part of the drive system. An extension shaft with compatible male and female ends can be inserted between the sponge mount and the head receiver, just like using an extension shaft in a socket wrench set.

An alternative configuration of the head receiver and drive system places an adjustable head receiver at the distal tip of the eyelid care appliance, and the head angle can be adjusted through a range up to 180 degrees (i.e., +90-degree head angle to −90-degree head angle) and fixed at a given head angle through detents and/or locking mechanism. Such expanded range of head angles avoids the need to invert the eyelid care appliance when cleaning the upper eyelid margins, and also keeps the on/off button in the same location within the user's grip. An adjustable head receiver embodiment of the eyelid care appliance facilitates different angulations of treatment and therapy. A preferred adjustable head receiver embodiment has detents in the head receiver at specific angulations, e.g., 45, 90, 135 and 180 degrees of head angle. The head can be locked in place at each detent position. A second preferred adjustable head receiver embodiment can be locked in place, e.g. by a clamping means, at any angulation with the range of head angulation.

As shown in FIG. 1d, a battery 8 is fitted in a battery compartment in the proximal end of the main housing 1. Battery access is through a battery door 3. Housing cap 4 seals the proximal end. A DC motor 7 with a pinion gear 13 on its output shaft drives a spur gear linkage 14 that converts rotary motion of the pinion gear 13 to oscillating (reciprocally arcuate) motion and drives a keyed shaft 15. The keyed shaft 15 causes the head receiver 6 to oscillate. The sponge mount 5 with affixed sponge fits firmly (either by friction or by detent) or preferably bristlebrush or Soft-Tip 200 into a head receiver 6 and oscillates in a fixed relationship to the head receiver 6. If a rechargeable battery is used as the power source in the handpiece, a means of recharging the battery (e.g., inductive, or conductive terminals), can be incorporated into a stand or holder for the device of the invention; alternatively, the battery can be removed through battery cover 3 for recharging in a charging dock.

In a preferred embodiment for SA Cleaning and SP Cleaning, the eyelid care appliance comprises a drive module, drive controls and annunciator, eyelid care module with adjustable head angle, proximity sensor, proximity controls and annunciator, and related data channels. The proximity sensor determines or depicts the distance between the surface of the head and the eyelid margin. The proximity annunciator can be a light or a light array, a display, a generated voice, or tactile. A preferred configuration, as shown in FIGS. 18a, 18b, and 18c, of proximity sensor and annunciator, is a video camera 44 linked to a smartphone or tablet computer with display (collectively, "smart device") that is paired with the eyelid care appliance by NFC; the video image from the eyelid care appliance is transmitted through NFC and displayed on the smart device. The video camera 44 is preferably on a small gooseneck that can slide within a yoke or be detached from the yoke to change the point of view of the video camera. As shown in FIG. 18c, a user of the eyelid care appliance with video proximity system "lands" the head on the eyelid and moves the head along the eyelid during cleaning of the eyelid. This preferred embodiment comprises a power supply, motor, drive system that transmits motive force from the motor to oscillate a head receiver, motor controls, a proximity system, and proximity annunciator contained in a housing, wherein a head is detachably mated with the head receiver and protrudes from the housing and oscillates when the motor is powered on, wherein the proximity system is a video camera with lens mounted near the head and in near field communication with a smart device, and wherein the video output from the video camera is displayed on the smart device. By focusing on the smart device display linked to the eyelid care appliance by a near field communication channel, the user becomes immersed in control of the head rather than fearful of poking himself or herself in the eye. The proximity system can evaluate or score user performance as if the use of the eyelid care appliance were a video game.

Figure 2C:
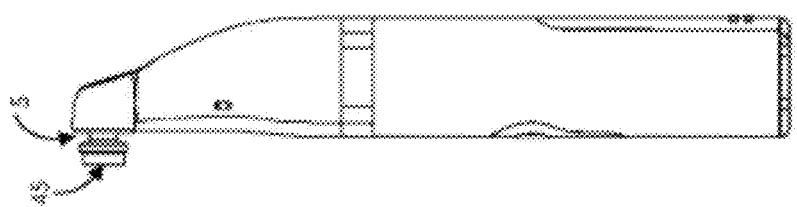
FIG. 2*c*: Eyelid Care Appliance, Integral Version, Side View
Figure 2B:
FIG. 2*b*: Eyelid Care Appliance, Integral Version, Front View
Figure 2A:
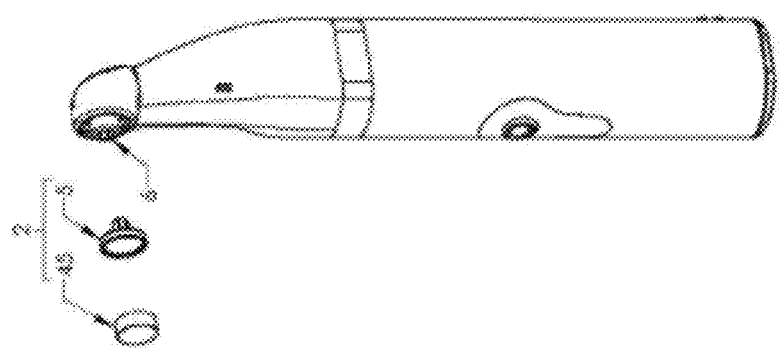
FIG. 2*a*: Eyelid Care Appliance, Integral Version, Exploded View with Head Detached from Receiver
Figure 9C:
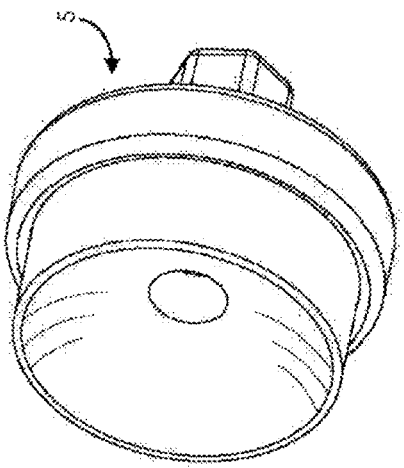
FIG. 9*c*: Concave Head Isometric View
Figure 9B:
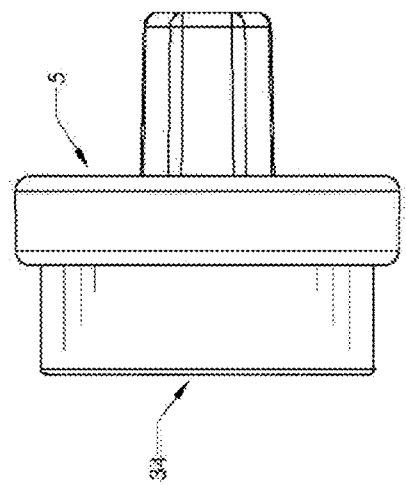
FIG. 9*b*: Concave Head Side View
Figure 9A:
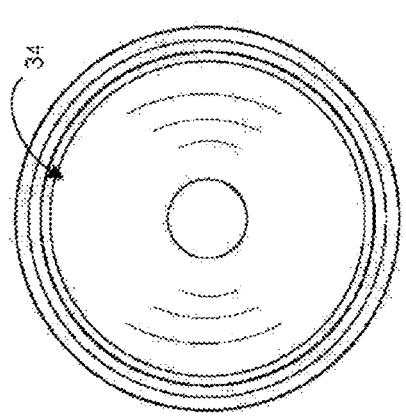
FIG. 9*a*: Concave Head Front View
Figure 11C:
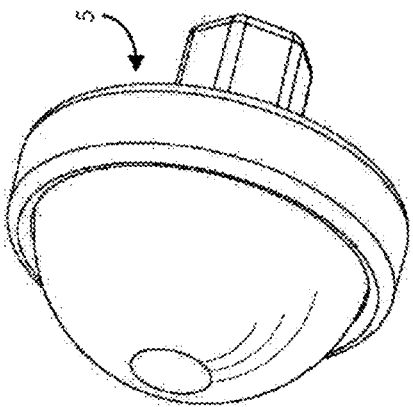
FIG. 11c: Convex Head Isometric View
Figure 27:
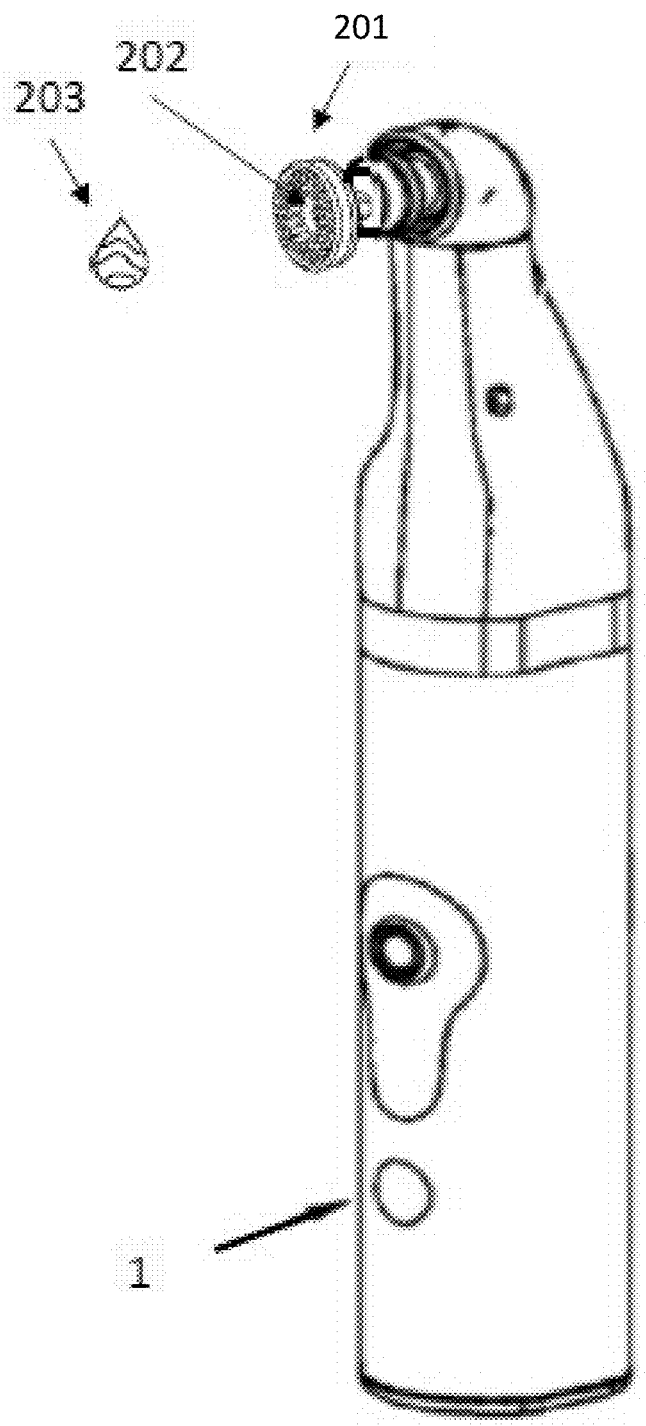
FIG. 27: shows a bristlebrush with recessed tip or hollow cavity.
Figure 28:
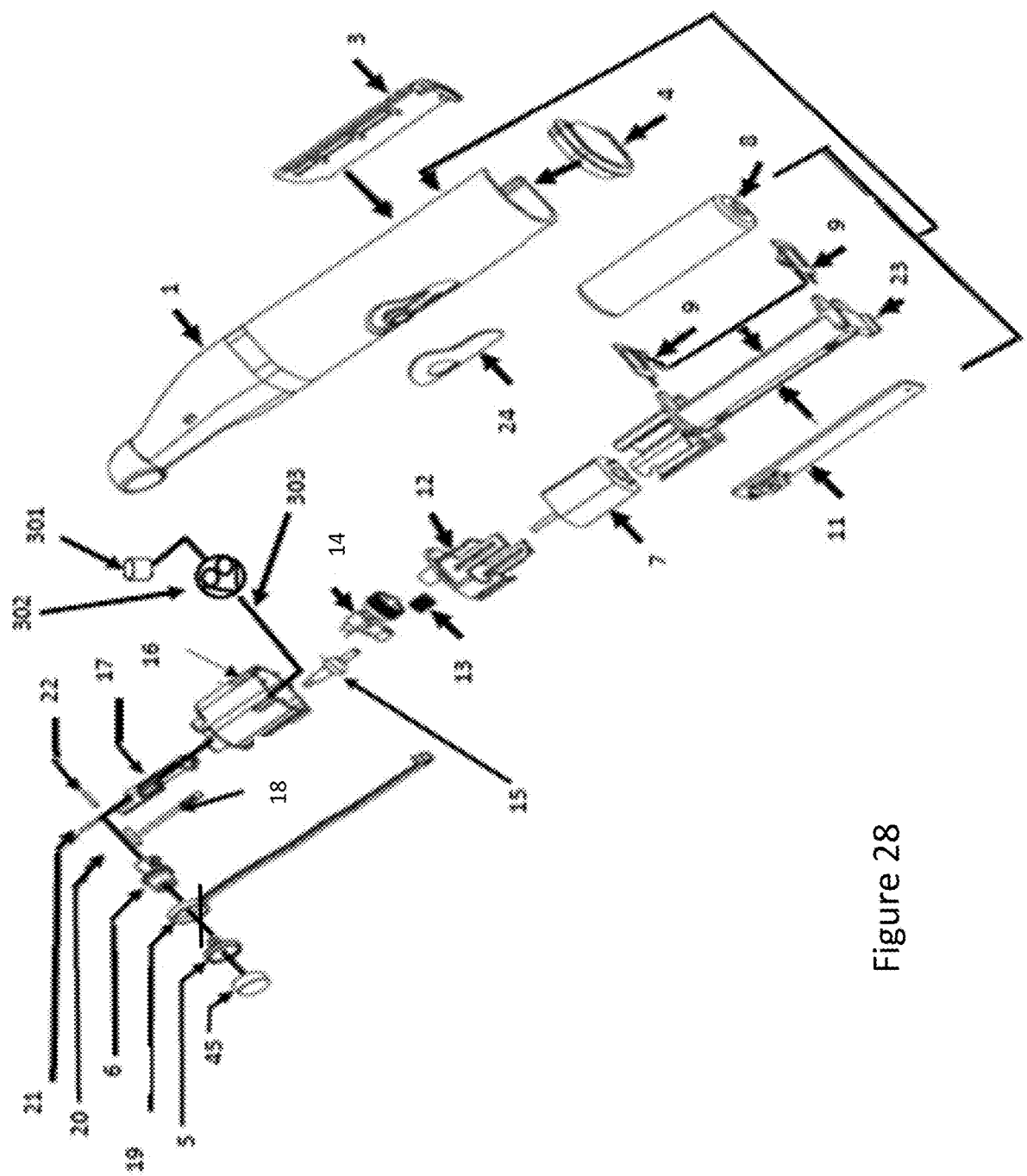
FIG. 28: shows alternative arrangement of a system of the invention with a pump.

As shown in FIG. 2a, a sponge mount 5, bearing a bristlebrush 200, is detachably (aka removably) affixed to the head receiver 6. The sponge mount 5, preferably has a polygonal post, is inserted into a socket on the head receiver 6. The head receiver 6 is linked to the distal end of the drive system and driven in an oscillating motion by the drive system. The post/socket fastening system facilitates the easy attachment and removal of a head. Disposable heads are inexpensive, yet can be distributed sterile in packages. Multiple use heads, for specific clinical procedures, are durable enough to withstand being autoclaved or otherwise repeatedly sterilized. The device of the invention has several alternative embodiments with fluid reservoirs of different types. The simplest design equipped with a fluid reservoir uses a head in which the head has a recessed tip or hollow cavity (called a "concave head"), shown in FIGS. 9a-9c, with a concave sponge 34 or a recess or hollow cavity 202 as shown in FIG. 27. The reservoir as shown in FIG. 28 would express liquids, gels, ointments, cleansers, solvents, gases, powders or other fluid or fluidizable medicaments held in the reservoir 301 using either pressure of a pump 302 using hose 303. The processes increase circulation and help to repair the skin which improves the treatment.

A preferred gel would contain Argan oil, Pomegranate Fruit Extract, Norway Spruce tree sap (Picea Abies Extract), and Jojoba Esters. The gel can be formulated from Aqua, Glycerin, 1,2-Hexanediol, Argania Spinosa (Argan) Kernel Oil, Punica Granatum (Pomegranate) Fruit Extract, Picea Abies Extract, Hydrolyzed Jojoba-Esters, Butylene Glycol, Polysorbate 20, Acrylates/C10-30 Alkyl Acrylate Crosspolymer, Hydroxyacetophenone, Sodium Hydroxide.

Argon Oil—Packed full of hydrating essential fatty acids and anti-inflammatory vitamin E and sterols, Argan oil is a nutrient powerhouse.

Pomegranate Fruit Extract—Is known for cell regeneration and helps to protect the epidermis.

Norway Spruce tree sap (Picea Abies Extract)—A pharmaceutical grade ingredient in Finland for various applications. This ingredient is extremely unique and provides anti-inflammatory, antioxidant, wound healing, and anti-bacterial properties.

Jojoba Esters—Derived from the seeds of a desert shrub, this oil is an emollient ester with excellent spreading, lubricating and penetrating properties However, the head could also be configured as a bristlebrush or Soft-Tip 200 and the recessed tip or hollow cavity 202 as shown in FIG. 27 which would allow for liquids, gels and ointments 203 to alternatively be deposited on the bristlebrush or Soft-Tip 200 in recess or hollow cavity 202. The deposited liquids, gels and ointments in the recess of the tip can then be applied to the eyelid surface when the device of the invention is in use. The hollow cavity 202 is located concentric with the primary axis through the center of the head face of the bristlebrush or Soft-Tip 200. The patient applies the topical agents for liquids, gels, ointments, cleansers, solvents, gases, powders or other fluid or fluidizable medicaments 203 and to the bristlebrush or Soft-Tip 200 hollow cavity 202, and applies the bristlebrush or Soft-Tip 200 to the outer surface of the eyelid, and engages the DC motor 7, which causes the bristlebrush or Soft-Tip 200 to oscillate, and scrubs the eyelid and underlying meibomian glands. The patient can reapply the topical agents if there is a need to treat the patient's eyelid and meibomian gland orifices. The topical agents are dissipated from the bristlebrush or Soft-Tip 200 by the oscillating scrubbing action.

Figure 7B:
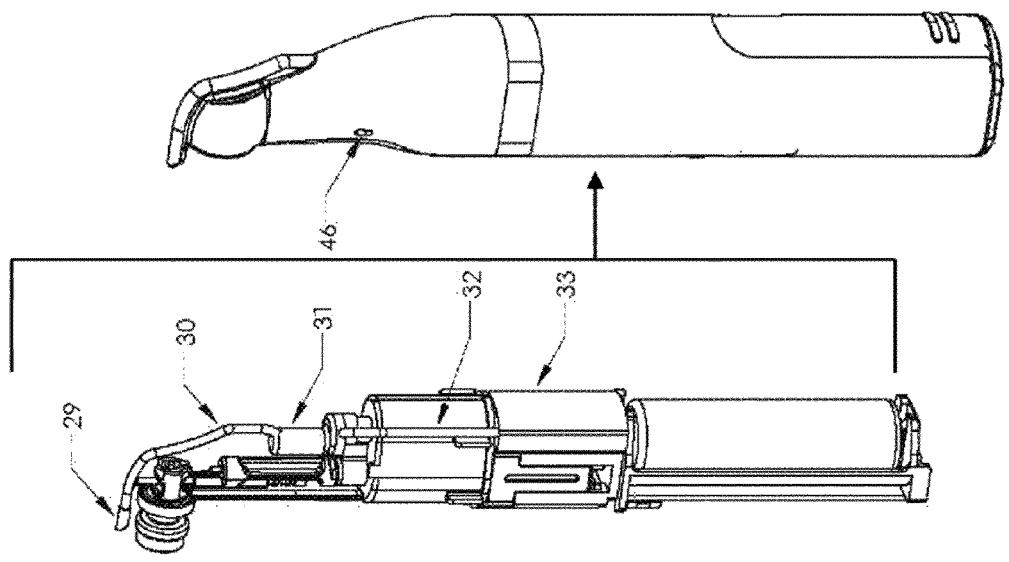
FIG. 7*b*: Eyelid Care Appliance, Integral Version, Liquid/Gas Pump Embodiment Exploded View
Figure 7A:
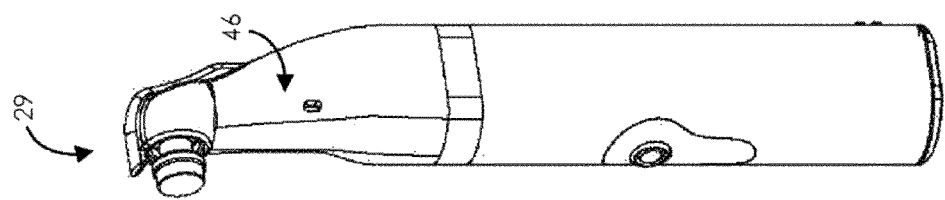
FIG. 7*a*: Eyelid Care Appliance, Integral Version, Liquid/Gas Pump Embodiment Front Isometric View

Another embodiment of the device of the invention, as shown in FIGS. 7a and 7b, features a fluid reservoir 33 and a pump 31 and supply channel 30 and 32 that connect the reservoir to a nozzle 29 near (or alternatively, ported through) the head 2. FIG. 28 shows an alternative arrangement of a system of the invention with a pump 302, tube 303 and reservoir 301 which feeds liquids, gels, ointments, cleansers, solvents, gases, powders or other fluid or fluidizable medicaments to the recess 202 in bristlebrush or Soft-Tip 200.

Figure 10C:
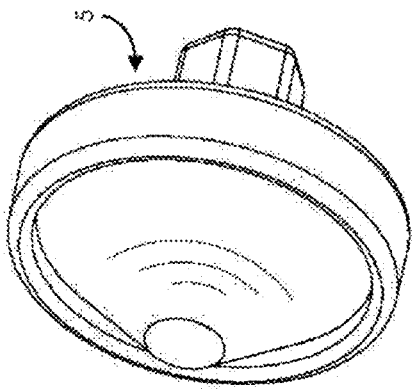
FIG. 10c: Pointed Head Isometric View
Figure 10B:
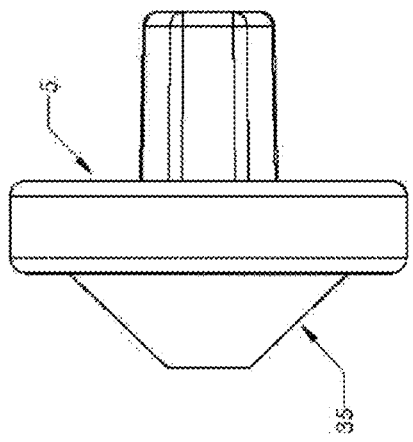
FIG. 10b: Pointed Head Side View
Figure 11B:
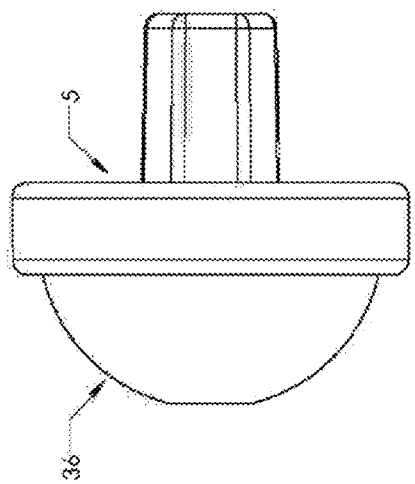
FIG. 11b: Convex Head Side View
Figure 10A:
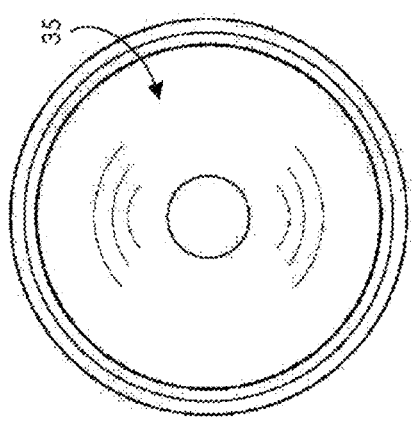
FIG. 10*a*: Pointed Head Front View
Figure 11A:
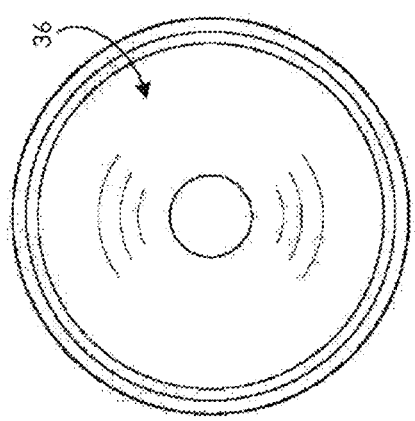
FIG. 11a: Convex Head Front View
Figure 12A:
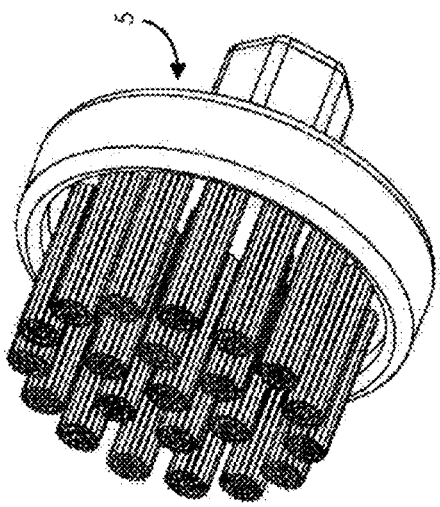
FIG. 12a: Bristle Head Front View
Figure 12A:
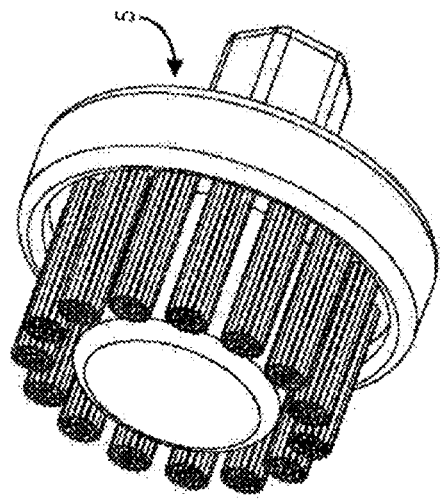
Figure 12A:
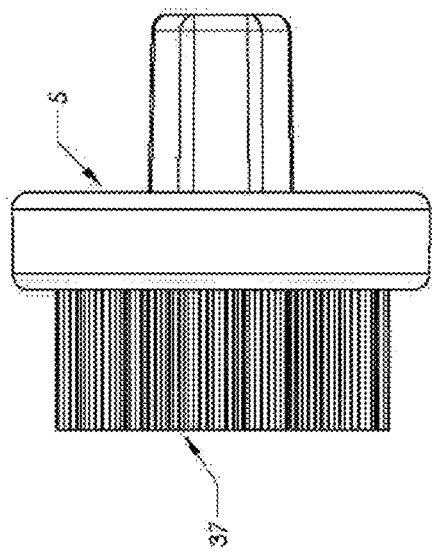
Figure 12A:
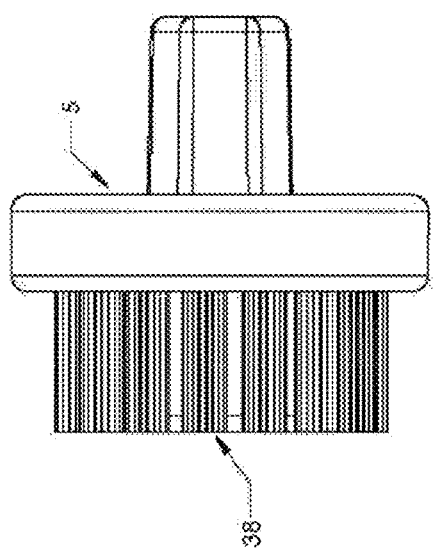
Figure 12A:
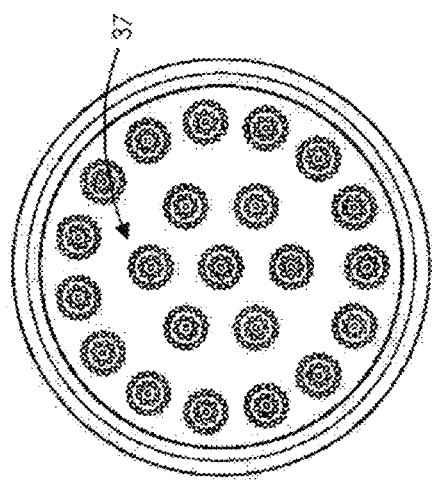
Figure 13A:
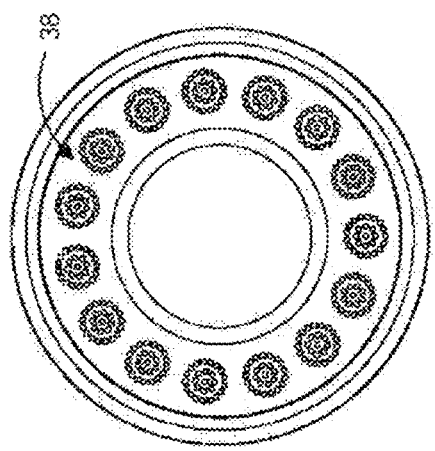
FIG. 13a: Bristle Head Front View
Figure 14C:
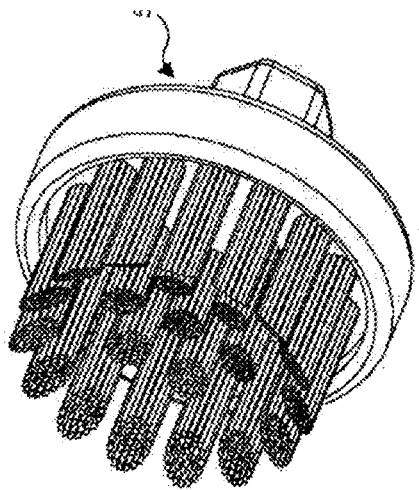
FIG. 14c: Concave Bristle Head Isometric View
Figure 15C:
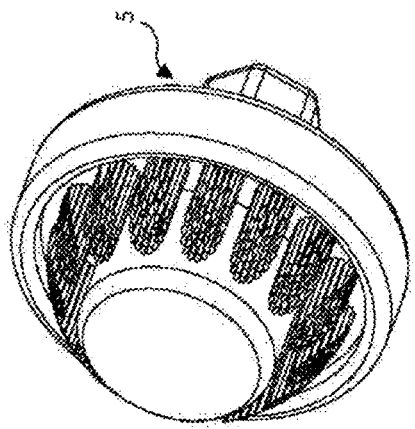
FIG. 15c: Convex Bristle Head Isometric View
Figure 14B:
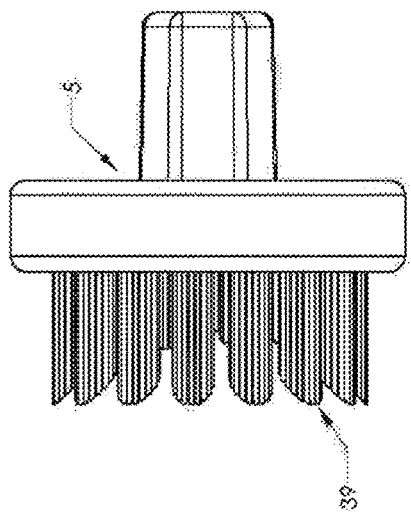
FIG. 14b: Concave Bristle Head Side View
Figure 15B:
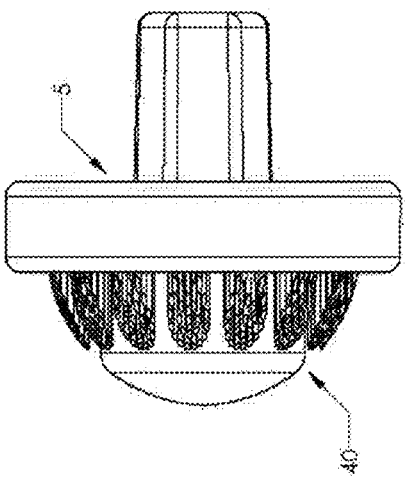
FIG. 15b: Convex Bristle Head Side View
Figure 14A:
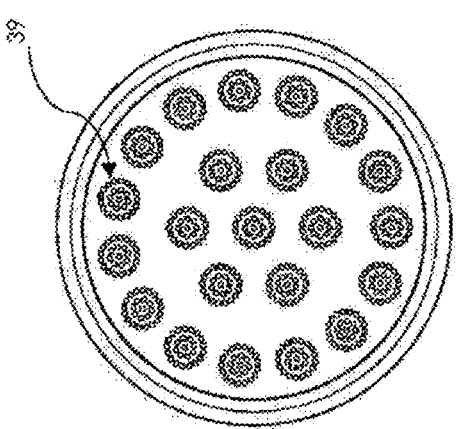
FIG. 14a: Concave Bristle Head Front View
Figure 15A:
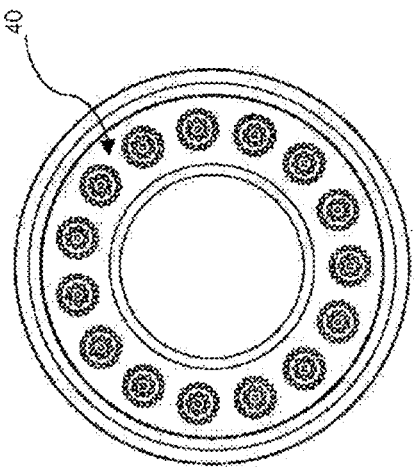
FIG. 15a: Convex Bristle Head Front View
Figure 16C:
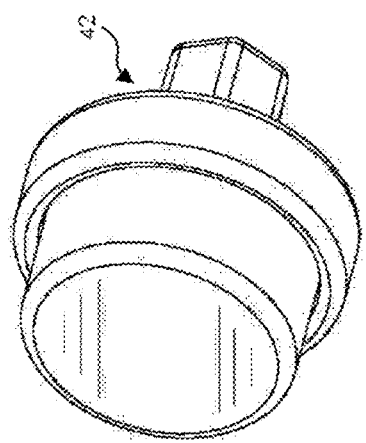
FIG. 16c: Reduced Diameter Head Isometric View
Figure 17C:
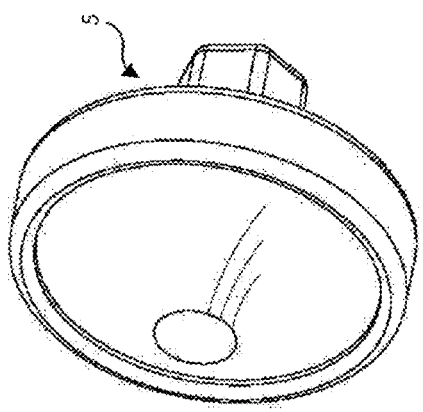
FIG. 17c: Caldera Head Isometric View
Figure 16B:
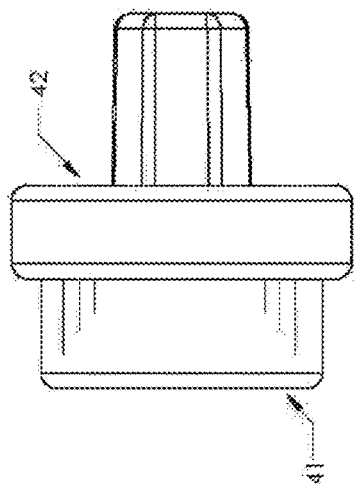
FIG. 16b: Small, Higher Chamfer Head Side View
Figure 17B:
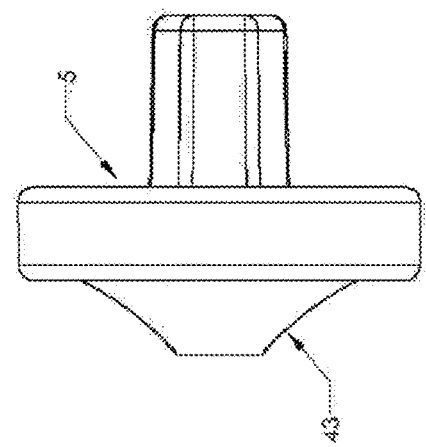
FIG. 17b: Caldera Head Side View
Figure 16A:
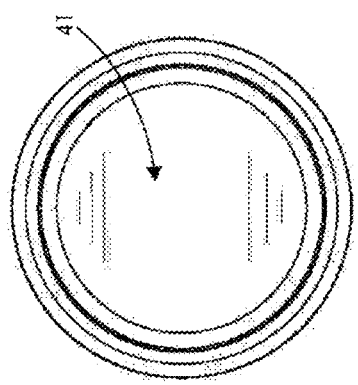
FIG. 16a: Small, Higher Chamfer Head Front View
Figure 17A:
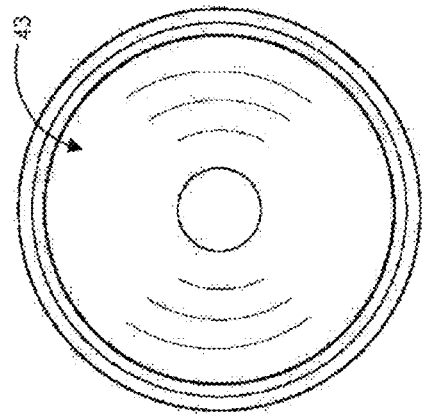
FIG. 17a: Caldera Head Front View

Embodiments of the eyelid care appliance with reservoirs are equipped with dispensing controls and associated sensors, valves, and optional data channels that report sensor output and valve status. Controls in the eyelid care appliance are activated by buttons on the housing (or handpiece) and implemented by a processor on a printed circuit board 11 in FIG. 3. Liquids, gels, ointments, cleansers, solvents, gases, powders or other fluid or fluidizable medicaments are placed in the reservoir for delivery to or near the head through the supply channel. The pump 31 forces the contents of the reservoir into or near the head for dispersal on the eyelid being cleaned or treated. Dispensed fluids can include cleaning agents, betadine, antiseptics, antimicrobials, anti-inflammatories, anesthetics, saline solution, water, solvents, taggants, stains, pharmaceuticals, nutraceuticals, and monoclonal antibodies. Reservoir and pump equipped embodiments can include a means to fluidize a powder or liquid into an aerosol for dispersal. An embodiment equipped to disperse liquids or gases can be equipped with a heater, to heat the liquid or gas, before dispersal near or through the head. Another embodiment equipped to disperse gases can use ambient air, preferably filtered by a filter in the air intake, rather than gas in a reservoir. This embodiment is particularly useful for administration of aerosols, since a separate gas reservoir is not needed. Heated fluids (liquid, gas, or air) can be used to warm the surface of the eyelid to "melt" blockages in meibomian glands, and the head (oscillating or inactive) can be used to massage blockage areas. A "massage" head would preferably have a convex sponge 35 (FIG. 10b) or conical sponge 43 (FIG. 17b). The drive module of an eyelid care appliance is either (i) in the same housing 1 as an eyelid care module, or (ii) interfaced with a detachable neck and a coupler, to transmit oscillating motion to the head receiver. A two-piece appliance can have all the structural elements and functionality of an integral eyelid care appliance other than the neck being detachable from a handpiece (e.g., a battery powered toothbrush).

Figure 3:
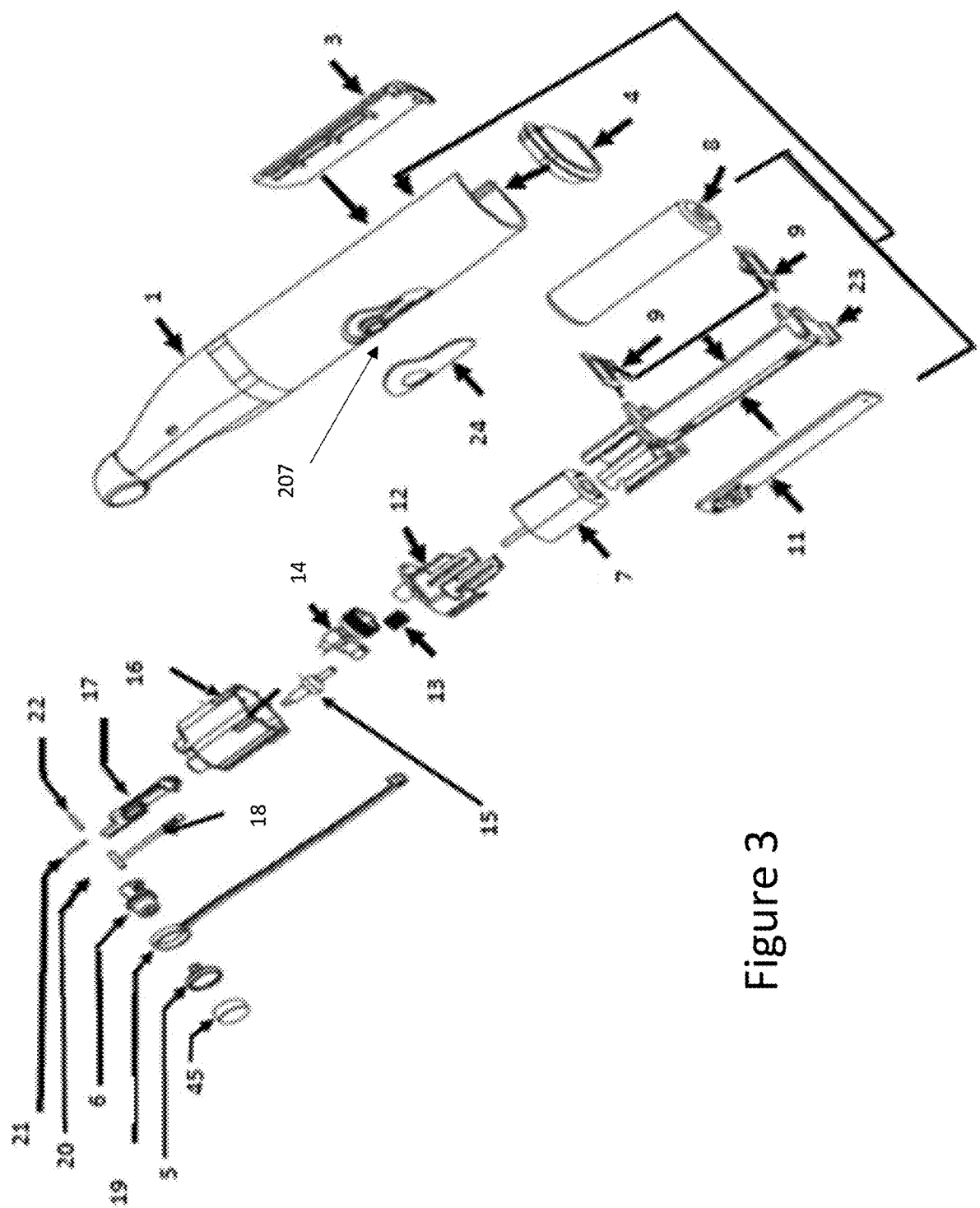
FIG. 3: Eyelid Care Appliance, Integral Version, Exploded View

As shown in FIG. 3, a battery 8 is fitted in a battery housing 23 in the proximal end of the main housing 1. Battery access is through a battery door 3. The battery contacts battery clips 9 to supply DC motor 7 with electrical power, with power controlled via printed circuit board 11, and a power button that is surrounded by a power button over-molding 24. Housing cap 4 seals the proximal end. A DC motor 7 with a pinion gear 13 on its output shaft, drives a spur gear linkage 14 that converts rotary motion of the pinion gear 13 to oscillating (reciprocally arcuate) motion and drives a keyed shaft 15. Pinion gear 13, spur gear linkage 14 and keyed shaft 15 fit within a drive housing 16. Receiver linkage 17 transmits the oscillating motion of the keyed shaft 15 through a linkage tee with spring 18 to the head receiver 6. Housing pin 20, linkage pin 21, and carrier pin 22 join the assembly of receiver linkage 17, linkage tee with spring 18, and head receiver 6.

The sponge mount 5 with affixed sponge 45 or more preferable bristlebrush or Soft-Tip 200 fits firmly (either by friction or by detent) into a head receiver 6 and oscillates in a fixed relationship to the head receiver 6. Light pipe and light ring 19 provide light in the direction of the head post axis from an LED 207 mounted on and controlled by printed circuit board 11. Alternatively, power controlled by printed circuit board 11 can be provided to LEDs near the head receiver 6 or to LEDs on the distal portion of the eyelid care appliance. If a rechargeable battery is used as the power source in the handpiece, a battery charger (e.g., inductive, or conductive terminals) can be incorporated into a stand or holder for the device of the invention; alternatively, the battery can be removed through battery cover 3 for recharging in a charging dock. One or more lighting LEDs can project light in front of the head, thereby providing adequate illumination for the user and/or a video camera.

Figure 19:
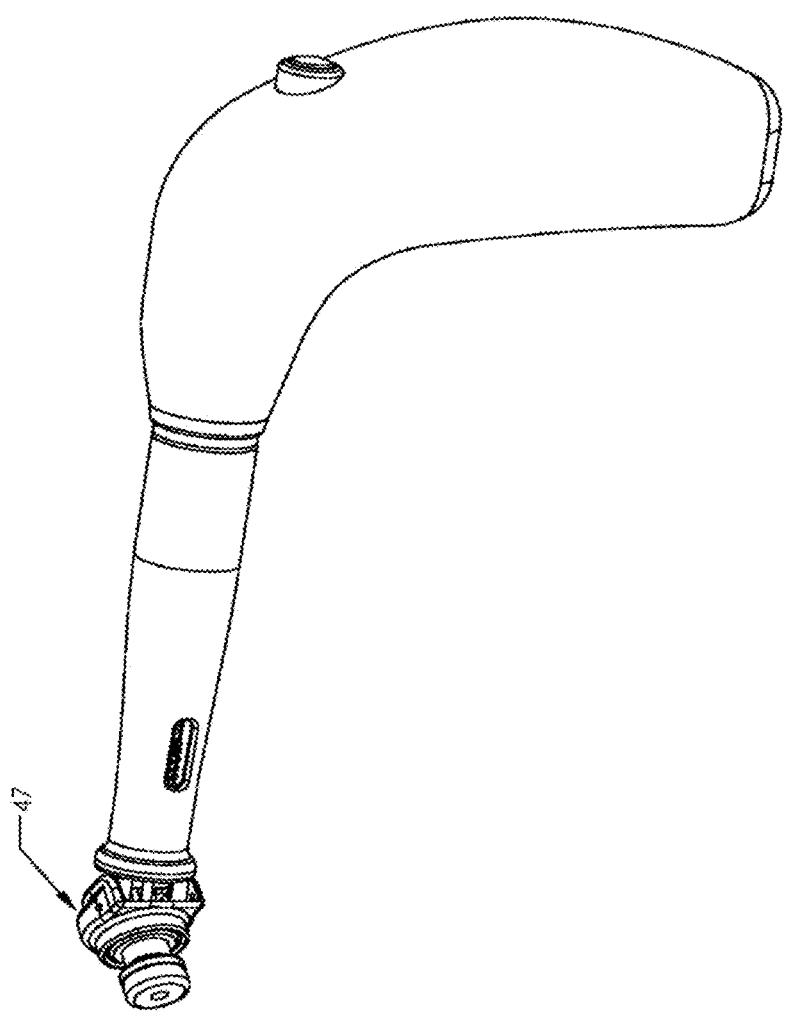
FIG. 19: Eyelid Care Appliance with Adjustable Head Angle and Pistol Grip.

As shown in FIG. 19, alternative embodiments of the eyelid care appliance include designs in which the appliance has a "pistol grip" proximal portion and adjustable head angle 47. Other alternative embodiments include (i) a "pistol grip" handpiece, (ii) versions in which the eyelid care appliance mounted on or integral with a glove, or (iii) in which the eyelid care appliance is mounted on a hand strap. The pistol grip integral embodiments can include a distal pivot so that the angle between the grip portion and the distal portion containing the eyelid care module (or in two-piece embodiments, the angle between the handpiece and the detachable neck) can be selected by the user and maintained by detents in the pivot mechanism or by a lock.

Figure 6B:
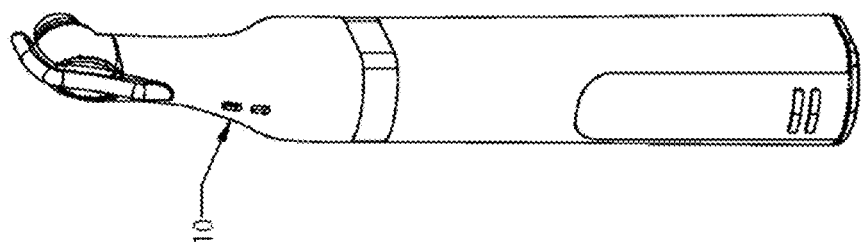
FIG. 6*b*: Eyelid Care Appliance, Integral Version, Suction Pump Embodiment, Rear Isometric View
Figure 6A:
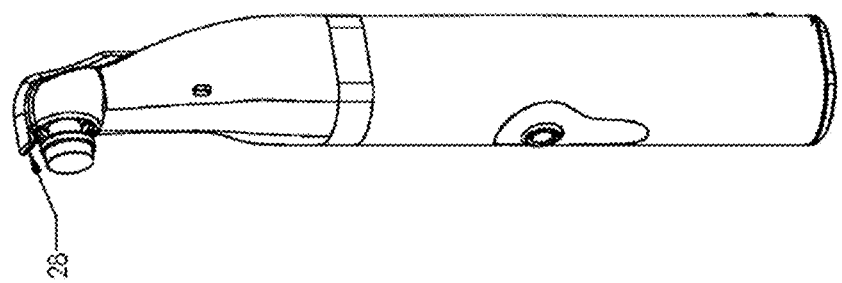
FIG. 6*a*: Eyelid Care Appliance, Integral Version, Suction Pump Embodiment, Front Isometric View
Figure 5:
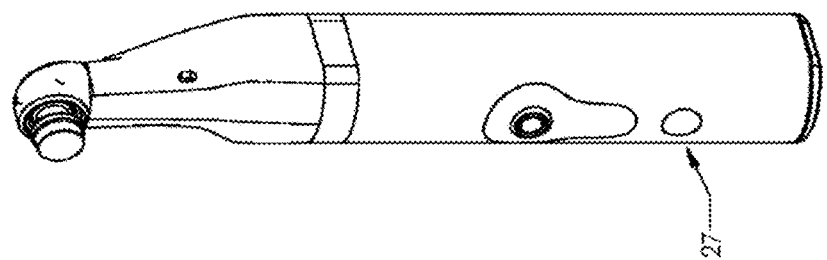
FIG. 5: Eyelid Care Appliance, Integral Version, LED Embodiment with LED Light Ring and Adjustment, Front Isometric View
Figure 4:
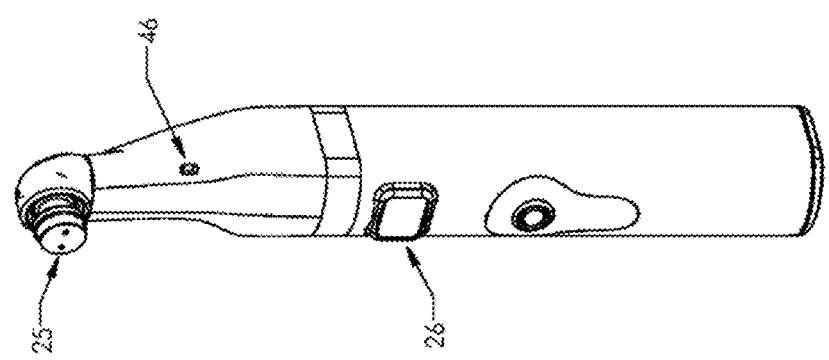
FIG. 4: Eyelid Care Appliance, Integral Version, LCD Embodiment, Front Isometric View

As shown in FIG. 4 (showing sensor 25), FIG. 5 (showing LED control 27), FIG. 6a (showing suction nozzle 28), FIG. 6b (showing suction pump outlet 10), and FIGS. 7a and 7b (showing liquid/gas nozzle 29, liquid/gas tubing 30 and 32, liquid/gas pump 31, and liquid/gas reservoir 33), various sensors, inlets, and outlets can be configured in the eyelid care appliance. FIG. 6a and b shows a suction pump with a suction inlet near the head and a suction pump outlet 10 in the housing, wherein the suction inlet removes debris and liquids from the eyelid margin and expels such debris and liquids as a waste stream through the outlet 10 in the housing. The outlet 10 can be configured with a connector and mated with connectorized tubing that routes the waste stream into a collection reservoir, diagnostic apparatus input, or a drain. A preferred embodiment further comprises a suction pump with a suction inlet near the head and an outlet in the housing, wherein the suction inlet removes debris and liquids from the eyelid margin and expels such debris and liquids as a waste stream through an outlet in the housing. In embodiments with a suction pump, the waste stream input or output of the suction pump can be examined by a video camera, flow cytometer, or other sensor and associated software to detect and report the contents of the waste stream, e.g., particle count, chemical profile (before cleaning, during cleaning, after cleaning, especially of tear film), presence of bacteria, etc. Stains, monoclonal antibodies, and other taggants can be administered and monitored as part of waste stream assays. A preferred embodiment further comprises a suction pump with a suction inlet near the head, and an outlet in the housing, wherein the suction inlet removes debris and liquids from the eyelid margin and expels such debris and liquids as a waste stream through an outlet in the housing and wherein the waste stream input or output of the suction pump is examined by a video camera, flow cytometer, or other sensor and associated software to detect and report the contents of the waste stream. This embodiment provides the first real-time reporting of tear film profile, the efficacy of eyelid cleaning, cleanser concentration, medicament concentration, etc., and provides a very important new tool in training, in diagnosis, and in monitoring therapeutic interventions.

As shown in FIGS. 8a through 17c, the sponge or other material mounted on a head for contact with a skin or wound surface can have various constituent materials and geometries adapted to the cleaning, therapeutic application, or assay to be conducted. Exemplary materials and geometries are concave head 34, pointed head 35, convex head 36, bristle head 37, bristle head with sponge 38, concave bristle head 39, convex bristle head 40, small, higher chamfer head 41, small, higher chamfer sponge mount 42, and conical head 43.

Figure 26:
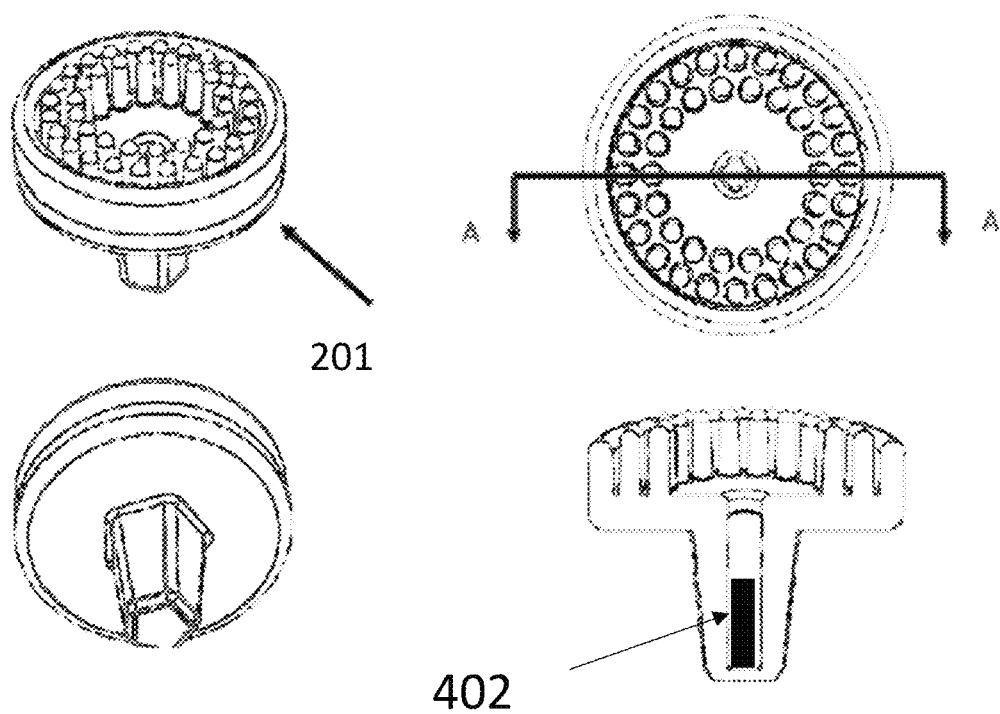
FIG. 26: preferred bristlebrush or Soft-Tip of the invention.

Furthermore, as noted FIG. 1a-d and FIG. 2a-c show perspective views and various views of the device of the present invention and the bristlebrush or Soft-Tip head 200. As shown in these figures, the present invention is a handheld device that is preferably battery charged. Thus, the invention comprises a handle/main housing 1, a bristlebrush or Soft-Tip 200, a battery 8. The bristlebrush or Soft-Tip 200 is placed over the eye (with the eyelid closed) and that provides a gentle massaging action to the eyelid. This gentle massaging action is caused by the oscillation of the bristlebrush or Soft-Tip 200. In a preferred embodiment, the bristlebrush or Soft-Tip 200 oscillates in an elliptical motion. FIG. 26 shows the most preferred embodiment of the invention Soft-Tip 201. Soft-Tip 201 is molded from flexible silicone and is has an insert 402 that allows it to be magnetically connected to the handle/main housing 1.

The main housing 1 preferably comprises a power button 24, which, in a preferred embodiment, allows the massaging action of the bristlebrush or Soft-Tip 200 to be activated either alone or in combination with heat. The main housing 1 also preferably comprises a light emitting diode (LED) 207. In a preferred embodiment, the LED 207 is a dual LED with both a green LED and a red LED in the same light. The green LED indicates that the batteries are being charged. The red LED indicates that the unit is heating the bristlehead or Soft-Tip. The main housing 1 can also have a selector switch which allows the patient to select cleaning modes comprising of a circular motion, an elliptical path or oscillating motion depending on the selected mode. The system can also be configured as a wired device or with a rechargeable battery and charger.

Alternatively, one could heat in head, by placing some conductive material/wires in the tips and utilize either AC or DC, current to heat the head. The device can also be configured to use electromagnetic induction to transmit electricity to sealed head thereby eliminating the need for conductors.

Alternatively, the invention can also use induction heating to heat the head.

In one embodiment, the motor shaft (not shown) of the motor 7 is connected to a flexible shaft 17, which extends from the top of the motor 7 to inside of the head receiver 6 so that as the motor shaft rotates, the flexible shaft 17 also rotates. In an alternate embodiment (not shown), two non-flexible shafts connected by a first universal joint could be used in lieu of the flexible shaft. In the latter embodiment, the first shaft would be connected to the motor shaft, and the second shaft would be connected to the oscillation assembly inside the head receiver 6. A second universal joint would be located at the point at which the second shaft connects to the oscillation assembly.

The bristlebrush or Soft-Tip 200 is preferably made of a soft elastomer or silicone. In a preferred embodiment, the bristlebrush or Soft-Tip 200 is shaped so as to be comfortable when placed over the eyelid.

In a preferred embodiment, the bristlebrush or Soft-Tip 200 is removable from the Main Housing 1.

The eyelid cleaning action occurs from the bristlebrush or Soft-Tip 200 being placed in communication with the patient's eyelid and the main housing 1 mechanisms causing the bristlebrush or Soft-Tip 200 to rotate in a circular motion or oscillate depending on the selected mode. The bristlebrush or Soft-Tip 200 can oscillate or follow an elliptical path.

It is the combination of the cleaning motion for the eyelid that the device provides, that allows it to provide stimulation for the meibomian glands. Alternatively, the bristlebrush or Soft-Tip 200 can also be heated which would provide additional stimulation to the meibomian glands. However, the heat needs to be limited from 75 to 104 degrees Fahrenheit so as not to harm the eyelid. When utilizing a heated bristlebrush or Soft-Tip 200, the main housing 1 contains a controller for modulating the heat of the bristlebrush or Soft-Tip 200.

Alternatively, the bristlebrush or Soft-Tip 200 or a round polymer head as shown in FIGS. 8a-c, 9a-c, 10a-c and 11a-c is fabricated from a soft polymer such as silicone, a soft elastomer, thermoplastic elastomer, silicone, mixture of silicone and thermoplastic elastomer, but any suitable medical grade soft polymer can be used. The bristlebrush or Soft-Tip 200 can also be formulated with an antimicrobial substance which is imbibed into the silicon, another erodible material, or soft plastic material that forms the bristlebrush or Soft-Tip 200. The use of a natural antimicrobial material would be a significant benefit to the patient. However, any antimicrobial substance which can be integrated into the silicon or soft plastic material, that forms the bristlebrush or Soft-Tip 200, would be appropriate such as silver, copper, and curcumin. The use of curcumin which has a well-documented history of having strong antimicrobial properties would be desirable because it is a natural product. To create a natural antimicrobial bristlebrush or Soft-Tip 200 utilizing curcumin one would mix 900 mg of curcumin with one teaspoon of fish oil, flax seed oil, olive oil, cannabidiol (CBD) or canola oil. The curcumin will dissolve in the oil. Curcumin readily dissolves in lipids and fat, so it dissolves in the oil. Next a concentration of 100 ug/ml to 5 mg/ml is effective against bacteria. That would be net constant release. Because curcumin is heat and light sensitive, the use of 5 to 10 times the concentration is recommended to make the bristlebrush or Soft-Tip 200. To accomplish the integration of the curcumin into the silicon at a concentration of 0.3-3.3 mg/ml the following process is used. Take the appropriate amount of the curcumin oil mixture needed to arrive at a 0.3-3.3 mg/ml mixture of curcumin and silicone and add it to the silicone mixing completely. Then utilize the mixture to mold the bristlebrush or Soft-Tip 200 followed by curing the bristlebrush or Soft-Tip 200 in an oven which is heated to 200 degrees C. and allow the bristlebrush or Soft-Tip 200 to cure for 4 hours or until the bristlebrush or Soft-Tip 200 is firm yet supple.

The addition of curcumin into the matrix of the bristlebrush or Soft-Tip 200 has antimicrobial properties, which will minimize the problems with transferring bacteria, which could affect the eye heath of the patient. The bristlebrush or Soft-Tip 200 is utilized by the patient applying the oscillating bristlebrush or Soft-Tip 200 on the distal end of the appliance, together with a solvent or cleanser to the eyelid, to scrub the eyelid and the meibomian glands on the edge of the eyelid.

Figure 22:
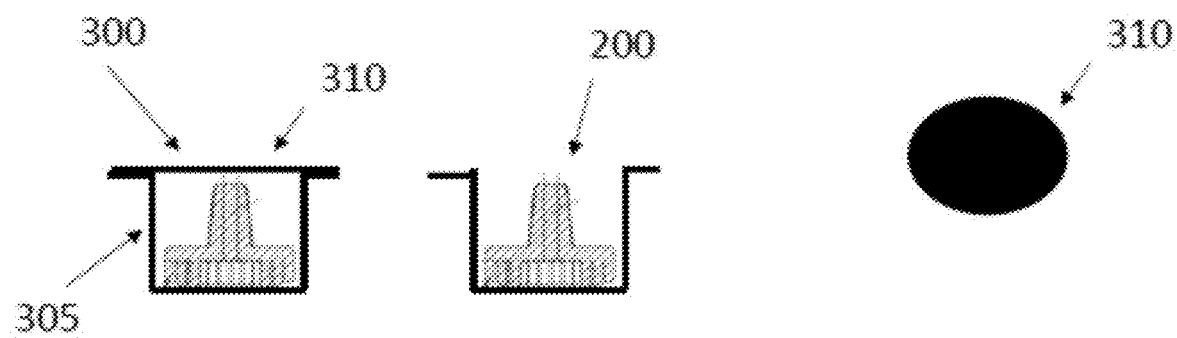
FIG. 22: is a view showing the bristlebrush or Soft-Tip in a packaging which is designed to eliminate the need for handling the unpackaged bristlebrush or Soft-Tip.

Alternatively, a package which minimizes the handling of the bristlebrush or Soft-Tip 200 by the patient would also minimize the problems of transferring bacteria which could affect the eye heath of the patient. The bristlebrush or Soft-Tip 200 can also be made of an antimicrobial material to further improve the sterile properties of bristlebrush or Soft-Tip 200. FIG. 22 is a view showing the bristlebrush or Soft-Tip 200 in a packaging which is designed to eliminate the need for handling the unpackaged bristlebrush or Soft-Tip 200. The package 300 is made from a plastic which is rigid enough to hold the bristlebrush or Soft-Tip 200 without damaging it during shipping. The package 300 could be formed as a single unit or as a series having 5-10 packages in a strip. The cup 305 supports the bristlebrush or Soft-Tip 200 and a heat activated or adhesive cover 310 is placed over the cup 305 to seal it. In the preferred embodiment the cover is formed from a material which would permit gas sterilization. The patient can use the package by removing cover 310 and then placing the head receiver 6 so that it is in communication with the bristlebrush or Soft-Tip 200 and attaching it by either magnetic, clasp or press fit means to the head receiver 6. The cup 305 could also include any antimicrobial material such as such as silver, copper, and curcumin.

Figure 24:
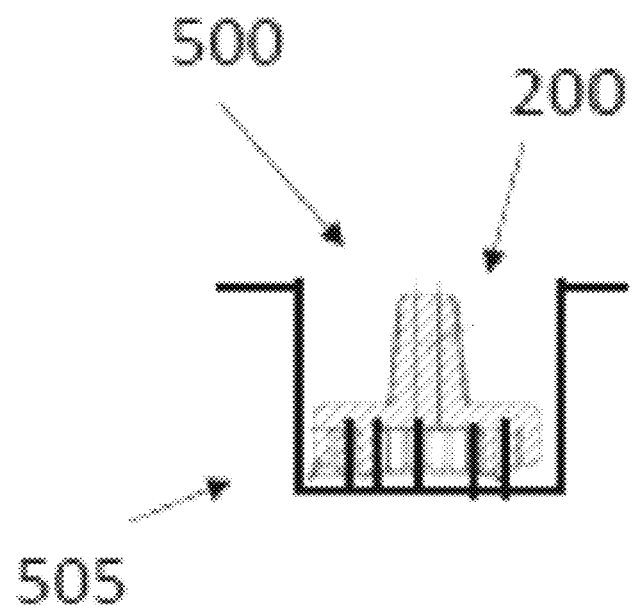
FIG. 24: integral manufacturing and shipping system.

An integral manufacturing and shipping system 500 shown in FIG. 24 is envisioned, where cup 505 could also act as the mold for the bristlebrush or Soft-Tip 200. The cup 505 would be formed in a reverse image of the bristlebrush or Soft-Tip 200 and the silicone or soft plastic would be deposited into the cup forming the bristlebrush or Soft-Tip 200, and the bristlebrush or Soft-Tip 200 would be cured in the cup 505 and sterilized and shipped in cup 505.

Figure 25:
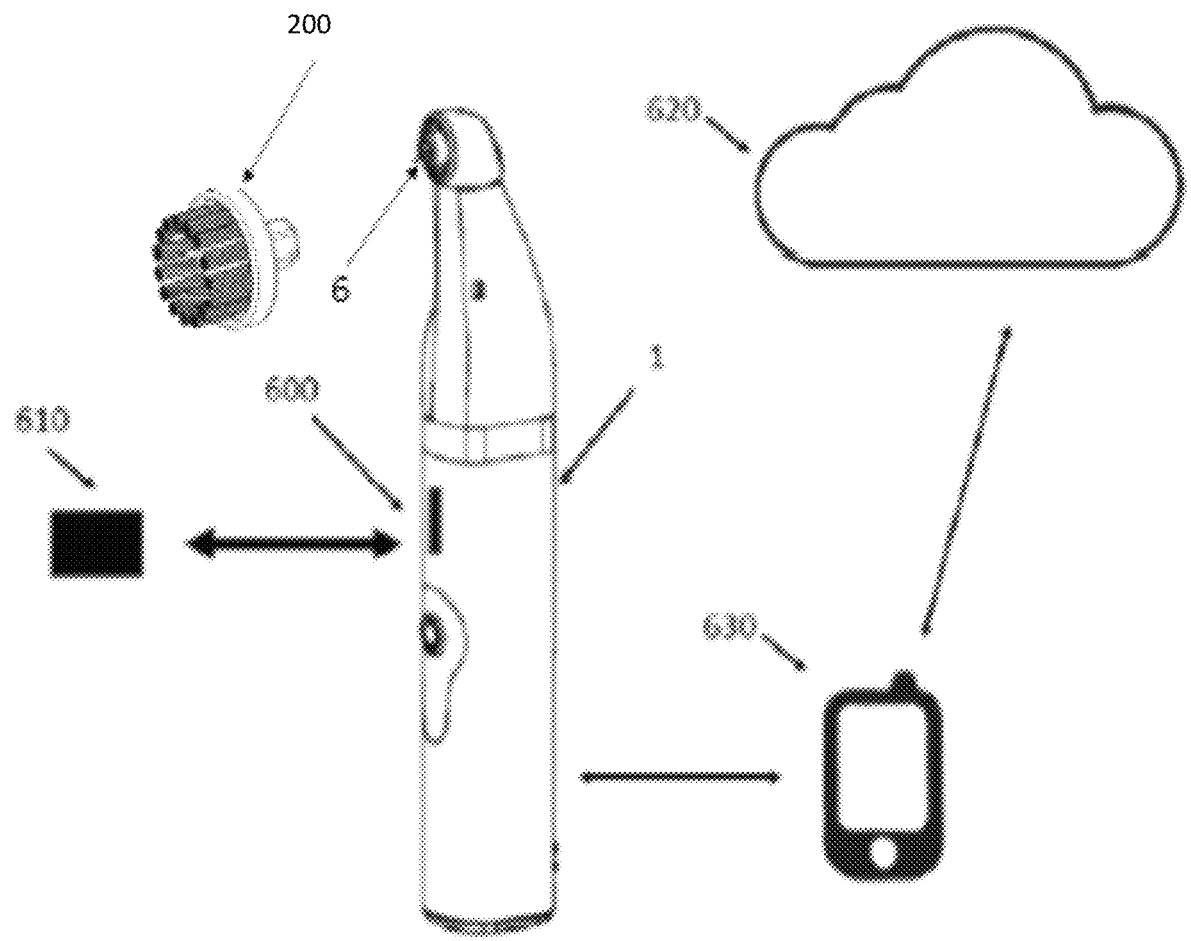
FIG. 25: smart chip expiration system.

Alternatively, the instant invention could also be a smart device by adding a WiFi, NFC, Bluetooth or a ZigBee interface which would collect data and provide it to a cloud database. The smart instant invention would communicate with an application loaded on a smart phone, tablet or computer and upload treatment times and pressures to an integrated cloud 620 application which could be shared with the healthcare provider to monitor treatments. The communication could be a means such as Zigbee, Bluetooth, Bluetooth BLE, ANT+, WiFi or NFC. The data that could be collected would be clinically significant such as treatment time, pressure and date. The collection of pressure data would require the integration of a pressure transducer into head receiver 6. You could also create a chip that comes with each head, which is a read writeable device as shown in FIG. 25. The chip 610 would be inserted into read slot 600 in the main housing 1. Without the chip the main housing 1 the smart device will not be activated. The chip would limit the utilization of the bristlebrush or Soft-Tip 200 to a set duration determined by the manufacturer. The device would work as follows: The patient would remove the bristlebrush or Soft-Tip 200 and attach it to the head receiver 6 and then remove the chip 610 from the package and insert it into read slot 600 in the main housing 1. The smart device would then communicate with the smart phone, tablet or computer 630 and set a timer on the cloud 620 or on the smart phone, tablet or computer application associated with the smart device. The smart phone, tablet or computer 630 would enable the smart device control system, which would allow the system to be powered on. The smart device would clear the chip, therefore eliminating the ability to reuse it. When inserted and active, the smart device would be enabled to use the bristlebrush or Soft-Tip 200 for the duration set by the manufacturer. The cloud or the smart phone, tablet or computer would reset the timer therefore preventing the patient from using the bristlebrush or Soft-Tip 200 after it is expired. The communication could be a means such as Zigbee, Bluetooth, Bluetooth BLE, ANT+, WiFi or NFC.

Software applications and sensors used with embodiments of the eyelid care appliance (including embodiments with a system on a chip within the eyelid care appliance or with a smart device linked by a communication method such as Zigbee, Bluetooth, Bluetooth BLE, ANT+, WiFi or NFC to the eyelid care appliance), can detect and report: how often and for how long one has scrubbed an area, battery condition, how much pressure is applied at the head, patency of the meibomian glands, health of the eyelid margin, etc. A video and/or sensor equipped eyelid care appliance can also provide images and/or assay reports of other body surfaces, e.g., skin lesions, wounds. The software applications can run on a computer integral with the eyelid care appliance, on a remote device, or on networked devices, including the eyelid care appliance as a client in a network.

Embodiments of the invention with lighting and a video proximity system can be equipped with band-limited light sources, either by selection of LED emitters and/or by filtering, and with multispectral image analysis software. Such an embodiment further comprises one or more band-limited light sources that project light in front of the head, wherein the proximity system is a video camera with lens mounted near the head and in near field communication with a smart device, wherein the video output from the video camera is fed to multispectral image analysis software in the smart device or in the appliance, and the output of the multispectral image analysis software is displayed on the smart device. Using multispectral image analysis well known in the art and implemented in software applications running on an integral processor or on a smart device with an NFC link to the eyelid care appliance, provides a non-invasive, real-time method of determining the health of an eyelid (or other skin area).

In addition to routine eyelid cleaning, SA Cleaning, and SP Cleaning, the invention may also be used to clean other areas and types of tissue where, or in other applications in which, a surface needs to be thoroughly cleaned, such as:

a. Pre-operative eyelid cleaning for ocular or peri-ocular surgery with cleansing/antimicrobial solutions (including povidone iodine solution).

b. Application of dermatologic creams for acne to be applied directly to the blemish or other skin area. This will allow a more precise placement of the medication so as not to dry out surrounding skin. Also, the oscillating sponge will allow a more even and thorough application of the product. The sponge can be pre-loaded with an appropriate amount of medication. Sensor-equipped embodiment of the invention can provide assay reports of the skin area.

c. Application of eyelash lengthening therapies, e.g., the Latisse® (Allergan Corp.) therapy, currently recommends the use of small applicator brushes to apply the product. This demands very exact eye-hand coordination. Use of the invention, preferably a video-equipped embodiment, would allow easier application with perhaps better coverage of the lashes.

d. Wound cleaning and debridement. Wound cleaning and debridement can be challenging by existing manual techniques. This device can be used to thoroughly and precisely clean wounds and remove foreign material and dead tissue from a wound. Sensor-equipped embodiment of the invention can provide assay reports of the skin area.

e. To apply a pharmaceutical to a lesion. Sensor-equipped embodiment of the invention can provide assay reports of the skin area.

f. Veterinary use for cleaning eyelids or other areas on animals that require a small cleaning device. Sensor-equipped embodiment of the invention can provide assay reports of the skin area.

The eyelid care appliance can be made in various sizes, e.g., pediatric and adult. An eyelid care appliance can be made in various sizes of drive module, e.g., different glove sizes, different pistol grip sizes, and in different sizes of head, e.g., pediatric and adult. Two-piece embodiments of the eyelid care appliance can be made with a standard interface between detachable neck and handpiece so that different sizes of detachable necks can be mated with different sizes of handpieces. Any embodiment of the eyelid care appliance can include an accelerometer that detects that the appliance has been dropped and that causes the motor to be powered off. Any embodiment of the eyelid care appliance can also use NFC to report its location to a smart device.

Alternative embodiments of the invention designed to care for body surfaces other than eyelids are called herein "surface care devices" and, like eyelid care appliances, comprise a drive module and an eyelid care module, and include the alternative embodiments described above (e.g., proximity systems, fluid and fluidized agent dispersal systems, suction systems and communication links to smart devices. The communication could be a means such as Zigbee, Bluetooth, Bluetooth BLE, ANT+, WiFi or NFC. etc.). Heads of various diameters and topologies are tailored to the skin area to be treated, e.g., a large concave head to treat elbows, a small concave head to treat fingertips. Surface care devices also include wound care devices adapted for various types of wounds to be cleaned or otherwise analyzed or treated using a surface care device; one embodiment of a surface care device for wounds is a mechanical debridement device.

A surface care appliance can be used for pre-operative scrubbing of small areas of skin before surgery, in particular for scrubbing of eyelid margins. Pre-operative scrubbing is currently done manually with swabs and sponges.

An alternative embodiment of the invention can be configured by choice of head to clean makeup off eyelids; a sterile head could be mounted for each use. Current methods of using moistened towelettes or cotton balls may not thoroughly clean eyelids of all residual makeup. This device could be used either primarily or as an adjunct to the above described methods to more thoroughly and rapidly remove eye makeup.

To generalize the preceding description, like eyelid care appliances, surface care devices of the invention are of two types: (1) an integral appliance, with an eyelid care module and drive module within a single housing, optionally with a pivoted grip, or (2) a two-piece appliance, comprising a handpiece and detachable head. Embodiments of surface care devices, e.g., for skin care and wound care, are adapted for areas to be cleaned or otherwise analyzed or treated.

The instant invention could be made more ergonomic. To do this, the design could include a head and Soft-Tip that protrudes further out from the handpiece and helps ensure easy contact with the eyelid margins.

The instant invention could also use a consumer replaceable and/or rechargeable battery.

The handpiece design could be designed such that it would be easier for arthritic patients to turn on/off. Such a design could include a larger grip and an improved switch.

The instant invention could also be made Waterproof. The design would have to account for the need to provide serviceability.

The instant invention could also include a redesign of the handpiece so that the shaft and the round plate currently a part of the bristlebrush or Soft-Tip become a permanent/semi-permanent part of the handpiece. This would reduce the cost of the Soft-Tip by making the tip and base plate reusable/semi-permanent.

It would allow the manufacturer to offer the bristlebrush or Soft-Tip in different lengths so as to provide a length most comfortable to the patient (and avoid a fixed redesign of the handpiece), allow press-on attachment of the bristlebrush or Soft-Tip to the handpiece and thus much easier for elderly patients to attach; reduce the size and weight of the packaging—hence reduce freight costs.

By attaching the plate to the shaft, it would allow for a Soft-Tip to be attached to the plate which is part of the handpiece.

Further modifications will also suggest themselves to those skilled in this art, and such are considered to fall within the spirit and scope of the invention as defined in the appended claims.

Although the preferred embodiment of the present invention has been shown and described, it will be apparent to those skilled in the art that many changes and modifications may be made without departing from the invention in its broader aspects. The appended claims are therefore intended to cover all such changes and modifications, as they fall within the true spirit and scope of the invention.

While various aspects and features of certain embodiments have been summarized above, the following detailed description illustrates a few exemplary embodiments in further detail to enable one skilled in the art to practice such embodiments. The described examples are provided for illustrative purposes and are not intended to limit the scope of the invention.

In the following description, for the purposes of explanation, numerous specific details are set forth in order to provide a thorough understanding of the described embodiments. It will be apparent to one skilled in the art, however, that other embodiments of the present invention may be practiced without some of these specific details. Several embodiments are described herein, and while various features are ascribed to different embodiments, it should be appreciated that the features described with respect to one embodiment may be incorporated with other embodiments as well. By the same token, however, no single feature or features of any described embodiment should be considered essential to every embodiment of the invention, as other embodiments of the invention may omit such features.

While certain features and aspects have been described with respect to exemplary embodiments, one skilled in the art will recognize that numerous modifications are possible. Further, while various methods and processes described herein may be described with respect to particular structural and/or functional components for ease of description, methods provided by various embodiments are not limited to any particular structural and/or functional architecture.

Hence, while various embodiments are described with or without certain features for ease of description and to illustrate exemplary aspects of those embodiments, the various components and/or features described herein with respect to a particular embodiment can be substituted, added, and/or subtracted from among other described embodiments, unless the context dictates otherwise. Consequently, although several exemplary embodiments are described above, it will be appreciated that the invention is intended to cover all modifications and equivalents within the scope of the following claims.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains, and which fall within the limits of the appended claims.

We claim:

1. A method of massaging, vibrating and cleaning eyelids of a patient's eye of cellular and sebaceous debris, wherein said massaging, vibrating and cleaning of the eyelids comprises the steps of:
    (a) the patient attaching a removable head to an eyelid care appliance, said eyelid care appliance having a main body with a housing having a longitudinal axis, a control, an instrumentation package, a battery, a motor, and a drive system;
    (b) said removable head having a primary axis through the center of a removable head face and said removable head face contacts said patient's eye, said removable head attaching to said main body such that the primary axis is inclined to the longitudinal axis of the body by an angle of between 20 degrees and 90 degrees;
    (c) said removable head having a hollow cavity concentric with the primary axis through the center of the removable head face;
    (d) said patient applies a topical agent to said removable head into said hollow cavity and said hollow cavity forms a reservoir that captures said topical agent during said massaging, vibrating and cleaning;
    (e) said drive system transmitting motive force from said motor to oscillate said removable head;
    (f) accessing the eyelids of said patient with said removable head such that said topical agent is applied to the eyelids of said patient;
    (g) oscillating the removable head wherein said oscillation has an oscillation frequency of 7,000 to 9,000 strokes/minute and said oscillation comprises repeating circular rotation up to a first angular amount in a first direction around the primary axis of the removable head, and circular rotation up to a second angular amount in a second opposite direction around the primary axis of the removable head such that the removable head does not make a full revolution resulting in an angular sweep of the head that is nominally 70 degrees; and
    (h) contacting said removable head face to said eyelid of said patient to massage the eyelids and to clean said eyelids and said meibomian gland, and to massage the long axis of the embedded meibomian gland through the eyelids such that the reservoir provided by the cavity helps maintain lubricity during the treatment by capturing lubricant which would otherwise escape during said massaging, vibrating and cleaning of the eyelids.

2. The method of claim 1 wherein said topical agent is selected from the group consisting of liquids, gels, ointments, cleansers, solvents, gases, powders and fluidizable medicaments.

3. The method of claim 1 wherein the removable head comprises a material selected from the group of a thermoplastic elastomer and silicone having at least one active ingredient added into the matrix of said material such that said at least one active ingredient is applied to the eyelid surface when the head is used for massaging, vibrating and cleaning the eyelids, wherein at least one active ingredient is selected from the group consisting of an anti-inflammatory, an aminoglycoside, and an anti-infective agent.

4. The method of claim 3 wherein said active ingredient is curcumin and said material is a thermoplastic elastomer, and wherein the curcumin is added into the matrix of the thermoplastic elastomer at a concentration of 0.4-9 mg/ml.

5. The method of claim 3 wherein said active ingredient is an anti-infective agent selected from the group consisting of silver, copper, amebicides, azole antifungals, echinocandins, polyenes and antiviral agents.

6. The method of claim 3 wherein said active ingredient is an aminoglycoside selected from the group consisting of paromomycin, tobramycin, gentamicin, amikacin, amikacin liposome, kanamycin, neomycin, paromomycin sulfate and plazomicin.

7. The method of claim 1 wherein said step of contacting said removable head face to said eyelid applies said removeable head to an outer surface of the eyelid.

8. A method of massaging and vibrating eyelids of a patient to liquify accreted meibum within Meibomian glands and cleaning eyelid margins of the patient's eye of cellular and sebaceous debris, the method comprising the steps of:
    (a) the patient attaching a removable head to an eyelid care appliance, said eyelid care appliance having a main body with a housing having a longitudinal axis, a control, an instrumentation package, a battery, a motor, and a drive system;
    (b) said removable head having a primary axis through the center of a removable head face, said removable head attaching to said main body such that the primary axis is inclined to the longitudinal axis by an angle of between 20 degrees and 90 degrees;
    (c) said removable head having a hollow cavity concentric with the primary axis through the center of the removable head face,
    (c1) said patient applies a topical agent to the hollow cavity;
    (d) said hollow cavity acts as a reservoir for said topical agent;
    (e) said drive system transmitting motive force from said motor to oscillate said removable head;
    (f) said patient accessing the eyelids with said removable head such that said topical agent is applied to said patient's eyelids;
    (g) said eyelid care appliance oscillating the removable head wherein said oscillation comprises repeating circular rotation up to a first angular amount in a first direction around the primary axis of the removable head, and circular rotation up to a second angular amount in a second opposite direction around the primary axis of the removable head such that the removable head does not make a full revolution; and (h) contacting said removable head face to said eyelids to massage said eyelids and clean said eyelid margins.

9. The method of claim 8 wherein the removable head comprises a thermoplastic elastomer having at least one active ingredient added into the matrix of said thermoplastic elastomer such that said at least one active ingredient is applied to the eyelid surfaces when the head is used for massaging and vibrating the eyelids, wherein said at least one active ingredient is selected from the group consisting of an anti-inflammatory, an aminoglycoside, and an anti-infective agent.

10. A method of massaging an eyelid and cleaning a margin of the eyelid and a meibomian gland orifice of a patient's eye of cellular and sebaceous debris, the method comprising the steps of:

attaching a removable head to an eyelid care appliance, the eyelid care appliance having a main body with a housing having a longitudinal axis, a control, an instrumentation package, and a drive system, the removable head having a primary axis through a center of a removable head face and having a hollow cavity concentric with the primary axis through the center of the removable head face;

pivoting the removable head in a frame with one or more detents to orient the removable head such that the primary axis is inclined at an angle ranging from about 20° to about 80° to the longitudinal axis of the housing;

applying a topical agent to the hollow cavity of the removable head, the hollow cavity forming a reservoir to capture the topical agent during use;

transmitting, via said drive system, a force to oscillate the removable head, the drive system comprising:
  a power supply;
  a motor electrically connected to the power supply; and
  a driveshaft having a first end connected to the motor and a second end connected to the removable head;

applying, via the removable head, the topical agent to the eyelid and the meibomian gland orifice;

oscillating the removable head wherein the oscillating repeats a first circular rotation up to a first angular amount in a first direction around the primary axis of the removable head and a second circular rotation up to a second angular amount in a second opposite direction around the primary axis of the removable head such that the removable head does not make a full revolution;

massaging, via the removable head face, the eyelid;

cleaning, via the removable head face, the margin of the eyelid and the meibomian gland orifice; and massaging, via the removable head face, along an entirety of a longitudinal axis of the meibomian gland orifice through the eyelid such that the reservoir captures the topical agent which would otherwise escape during the massaging of the eyelid and the cleaning of the margin of the eyelid.

11. The method of claim 10, wherein the topical agent is selected from the group consisting of a liquid, a gel, an ointment, a cleanser, a solvent, a gas, a powder, and a fluidizable medicaments.

12. The method of claim 10, wherein the removeable head comprises a material selected from the group of a thermoplastic elastomer and silicone having an aminoglycoside added into the matrix of said material such that the aminoglycoside is applied to the eyelid surface when the head is used for massaging and cleaning, wherein the aminoglycoside is selected from the group consisting of paromomycin, tobramycin, gentamicin, amikacin, amikacin liposome, kanamycin, neomycin, paromomycin sulfate and plazomicin.

13. The method of claim 10, wherein the removable head comprises silicone having an anti-infective agent added into the matrix of the silicone such that the anti-infective agent is applied to the eyelid surface when the head is used for massaging and cleaning.

14. The method of claim 13, wherein the anti-infective agent is selected from the group consisting of curcumin, silver, copper, amebicides, azole antifungals, echinocandins, polyenes and antiviral agents.

* * * * *